(12) United States Patent
Banner et al.

(10) Patent No.: US 8,158,655 B2
(45) Date of Patent: Apr. 17, 2012

(54) SULFONAMIDE DERIVATIVES

(75) Inventors: David Banner, Basel (CH); Harald Mauser, Schliengen (DE); Rudolf E. Minder, Ettingen (CH); Hans P. Wessel, Schliengen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 539 days.

(21) Appl. No.: 11/970,628

(22) Filed: Jan. 8, 2008

(65) Prior Publication Data

US 2008/0167348 A1 Jul. 10, 2008

(30) Foreign Application Priority Data

Jan. 10, 2007 (EP) .................................. 07100337

(51) Int. Cl.
*A61K 31/4427* (2006.01)
*A61K 31/38* (2006.01)
*C07D 333/52* (2006.01)
*C07D 409/02* (2006.01)

(52) U.S. Cl. ...................... 514/337; 514/443; 546/281.1; 549/53

(58) Field of Classification Search .................. None
See application file for complete search history.

(56) References Cited

U.S. PATENT DOCUMENTS

| | | | |
|---|---|---|---|
| 7,071,220 B2 | 7/2006 | Satoh et al. | |
| 2003/0229126 A1 | 12/2003 | Satoh et al. | |
| 2006/0116408 A1 | 6/2006 | Satoh et al. | |

FOREIGN PATENT DOCUMENTS

| | | |
|---|---|---|
| EP | 1325920 | 7/2003 |
| EP | 1486494 | 12/2004 |
| WO | WO 97/06802 | 2/1997 |
| WO | WO 97/49699 | 12/1997 |
| WO | WO 98/27081 | 6/1998 |
| WO | WO 02/22595 | 3/2002 |
| WO | WO 03/078419 | 9/2003 |
| WO | 2004/035047 | 4/2004 |
| WO | WO 2006/002133 | 1/2006 |
| WO | WO 2006/010629 | 2/2006 |
| WO | 2006/024779 | 3/2006 |
| WO | 2007/145835 | 12/2007 |
| WO | WO 2008/026046 | 3/2008 |
| WO | 2008/055068 | 5/2008 |
| WO | 2008/084261 | 7/2008 |
| WO | 2008/085608 | 7/2008 |

OTHER PUBLICATIONS

Bromidge et al., caplus an 1998:424243 (1998).*
Urata et al, caplus an 2005:177913.*
AmericanCynamid, caplus an 1966:43894.*
Dhatt et al., caplus an 1960:110579.*
Dhanoa et al., caplus an 1998:727783.*
Doggrell et al., Can. J. Physiol. Pharmacol., 83, pp. 123-130 (2005).
Lindstedt et al., Curr. Opin. Lipidol., 15, pp. 567-573 (2004).
Reed et al., J. Allergy Clin. Immunol., 114, pp. 997-1008 (2004).
Takai et al., Eur. J. Pharmacol., 501, pp. 1-8 (2004).
Takai et al., Trends Pharmacol. Sci., 25, pp. 518-522 (2004).
Takai et al., Curr. Vasc. Pharmacol., 1, pp. 217-224 (2003).
Raga et al., Eur. J. Med. Chem., 21, pp. 329-332 (1986).
Bromidge, S. et al, *Bioorg. & Med. Chem. Ltrs.*, vol. 11, p. 55-58 (2001).
XP002476238, Database Beilstein, Beilstein Instit. For Organic Chem.
XP002476239, Database Beilstein, Beilstein Instit. For Organic Chem.
XP002476240, Database Beilstein, Beilstein Instit. For Organic Chem.
XP002476241, Database Beilstein, Beilstein Instit. For Organic Chem.
XP002476242, Database Beilstein, Beilstein Instit. For Organic Chem.
XP002476243, Database Beilstein, Beilstein Instit. For Organic Chem.
Chilean Office Action in Corres. Appl. 47-2008.
Abstract of Columbia Patent CO4920231 corresponding to CL 2762-1997.

\* cited by examiner

*Primary Examiner* — Sun Jae Loewe
(74) *Attorney, Agent, or Firm* — George W. Johnston; Dennis P. Tramaloni; Erian C. Remy

(57) ABSTRACT

The invention is concerned with the novel sulfonamide derivatives of formula (I)

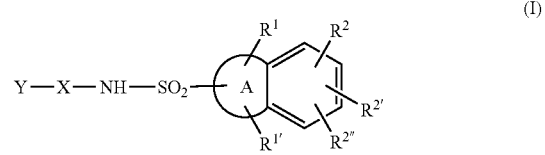

wherein A, $R^1$ to $R^{2'''}$, X and Y are as defined in the description and in the claims, as well as physiologically acceptable salts thereof. These compounds inhibit chymase and can be used as medicaments.

14 Claims, No Drawings

SULFONAMIDE DERIVATIVES

PRIORITY TO RELATED APPLICATION(S)

This application claims the benefit of European Patent Application No. 07100337.0, filed Jan. 10, 2007, which is hereby incorporated by reference in its entirety.

BACKGROUND OF THE INVENTION

Chymase is a serine proteinase with an expression pattern strictly limited to a sub-population of mast cells ($M_{CT}$ mast cell). Chymase is activated only upon mast cell activation and degranulation which restricts the enzyme activity to $M_{CT}$ positive tissues. Chymase specifically cleaves a number of pathologically relevant substrates (Raymond, W. W., S. W. Ruggles, et al.; JBC 2003 278(36): 34517-34524) whereby it can activate Angiotensin II, Endothelin, TGFb, Il1, SCF, collagenase and degrade proteins like Thrombin, FN, and APO A1,2. This pattern renders chymase an attractive target for allergic, inflammatory and fibrotic diseases. Indeed a number of successful animal studies with chymase inhibitors have demonstrated efficacy in atopic animals, vascular injury and atherosclerosis (Doggrell S A, Wanstall J C Can J Physiol Pharmacol. 2005 February; 83(2):123-30; Curr Opin Lipidol. 2004 October; 15(5):567-73; J Allergy Clin Immunol. 2004 November; 114(5):997-1008; Eur J. Pharmacol. 2004 Oct. 6; 501(1-3):1-8; Takai S, et al, Trends Pharmacol Sci. 2004 October; 25(10):518-22; and Curr Vasc Pharmacol. 2003 June; 1(2):217-24).

Thus, inhibition of chymase appears a useful modality in allergy, asthma, peripheral arterial occlusive disease, critical limb ischemia, vulnerable atherosclerotic plaque patients, unstable angina, congestive heart failure, left ventricular hypertrophy, ischemia reperfusion injury, cardiomyopathy, restenosis, rheumatoid arthritis, diabetic nephropathy, irritable bowel disease, Crohns' disease, and wound healing (burns/ulcers in Diabetes/CLI).

SUMMARY OF THE INVENTION

The invention is concerned with novel sulfonamide derivatives of formula (I):

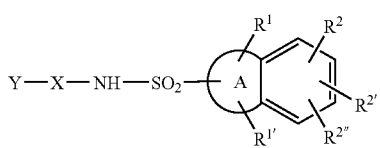

(I)

and pharmaceutically acceptable salts thereof, wherein A, X, Y, and $R^1$-$R^{2''}$ are as defined in the detailed description and claims. Further, the invention is concerned with a process and an intermediate for the manufacture of the above compounds, pharmaceutical preparations which contain such compounds, the use of these compounds for the production of pharmaceutical preparations as well as a process for the manufacture of the intermediate. The compounds of formula (I) inhibit Chymase. Thus, the present invention provides the novel compounds of formula (I) which are chymase inhibitors.

DETAILED DESCRIPTION OF THE INVENTION

Unless otherwise indicated, the following definitions are set forth to illustrate and define the meaning and scope of the various terms used to describe the invention herein.

The term "halogen" or "halo" means fluorine, chlorine, bromine or iodine. In preferred embodiments the halogen or halo is fluorine or chlorine with fluorine being most preferred.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, iso-propyl, n-butyl, s-butyl, and t-butyl. A $C_{1-4}$ alkyl (with one to four carbon atoms) is more preferred.

The term "halo $C_{1-6}$ alkyl", alone or in combination with other groups, means a $C_{1-6}$ alkyl in which one or more hydrogens have been replaced with the same or different halogens, such as —$CH_2Cl$, —$CH_2CF_3$, and trifluoromethyl. In preferred embodiments, the halogen portion of the halo $C_{1-6}$ alkyl is chlorine or fluorine.

The term "halo $C_{1-6}$ alkoxy", alone or in combination with other groups, means a $C_{1-6}$ alkoxy in which one or more hydrogens have been replaced with the same or different halogens. In preferred embodiments, the halogen portion of the halo $C_{1-6}$ alkoxy is chlorine, fluorine or bromine, with chlorine or fluorine being most preferred.

The term "acyl", alone or in combination with other groups, means —CO—$C_{1-6}$ alkyl.

The term "heteroalkyl" means a $C_{1-6}$ alkyl substituted by one or more substituents selected independently from the group consisting of nitro, hydroxy, halogen, cyano, $C_{1-6}$ alkoxy, formyl, $C_{1-6}$ alkylcarbonyl, carboxyl, $C_{1-6}$ alkylthio, $C_{1-6}$ alkyl sulfinyl, $C_{1-6}$ alkyl sulfonyl, amino and mono- or di-$C_{1-6}$ alkyl substituted amino. This term is further exemplified by such radicals as 2-hydroxyethyl, and perfluoromethyl.

The term "$C_{3-7}$ cycloalkyl", alone or in combination with other groups, means a saturated monovalent cyclic hydrocarbon radical of three to seven ring carbons. Examples include cyclopropyl, cyclobutyl, and cyclohexyl.

The term "$C_{1-6}$ alkoxy", alone or in combination with other groups, means the group R'—O—, wherein R' is a $C_{1-6}$ alkyl.

The term "$C_{2-6}$ alkenyl", alone or in combination with other groups, means a straight-chain or branched hydrocarbon residue comprising an olefinic bond, having two to six carbon atoms, such as, for example, ethenyl or 2-propenyl.

The term "$C_{2-6}$-alkynyl", alone or in combination with other groups, means a straight-chain or branched hydrocarbon residue comprising a triple bond, having two to six carbon atoms, such as, for example, ethynyl and 2-propynyl.

The term "$C_{0-6}$ alkylene" means a bond or a straight chain or branched divalent saturated aliphatic hydrocarbon group of 1 to 6 carbon atoms. Accordingly, the term "$C_0$ alkylene" means a bond.

The term "aryl", alone or in combination with other groups, means a phenyl or a naphthyl group. Preferably the aryl is a phenyl group.

The term "heterocyclyl", alone or combination with other groups, means non-aromatic mono- or bi-cyclic radicals of three to eight ring atoms in which one or two ring atoms are heteroatoms selected from N, O, or $S(O)_n$ (where n is an integer from 0 to 2), with the remaining ring atoms being carbon.

The term "heteroaryl" means a monocyclic or bicyclic radical of 5 to 12 ring atoms having at least one aromatic ring containing one, two, or three ring heteroatoms selected from N, O, and S, with the remaining ring atoms being carbon. Preferably, the attachment point of the heteroaryl radical will be on an aromatic ring.

The terms "optionally substituted aryl", "optionally substituted heteroaryl", "optionally substituted heterocyclyl" and "optionally substituted $C_{3-7}$ cycloalkyl" means, respectively aryl, heteroaryl, heterocyclyl and $C_{3-7}$ cycloalkyl optionally substituted by one or more substituents independently selected from the group consisting of halogen, nitro, cyano, amino, $C_{1-6}$ alkyl, $C_{2-6}$ alkenyl, $C_{2-6}$ alkynyl, hydroxy, $C_{1-6}$ alkoxy, heteroalkyloxy, mono- or di-$C_{1-6}$ alkyl substituted amino, acyl, formyl, heteroalkylcarbonyl, $C_{1-6}$ alkoxycarbonyl, heteroalkyloxycarbonyl and heteroalkyl.

Preferred radicals for the chemical groups whose definitions are given above are those specifically exemplified in the Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" includes such salts. Compounds of formula (I) in which a COOH group is present can further form salts with bases. Examples of such salts are alkaline, earth-alkaline and ammonium salts such as e.g. Na—, K—, Ca— and Trimethylammonium salt. The term "pharmaceutically acceptable salts" also includes such salts. Acid addition salts as described above are preferred.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

In reference to a particular group or molecule, the term "substituted" refers to the fact that at least one of the hydrogen atoms of that group or molecule is replaced by some other substituent.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 300 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Compounds that have the same molecular formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). Chiral compounds can exist as either individual enantiomers or mixtures thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art.

Unless otherwise indicated, the term "a compound of the formula" or "a compound of formula" or "compounds of the formula" or "compounds of formula" means any compound selected from the genus of compounds as defined by the formula.

In detail, the present invention relates to the compounds of formula (I):

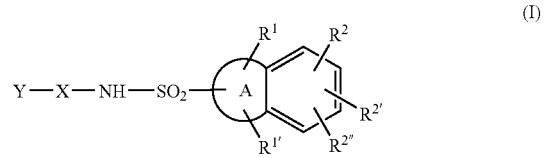

(I)

or pharmaceutically acceptable prodrugs or salts thereof, wherein:

A is selected from the group consisting of:
(1) a phenyl ring,
(2) a heteroaryl ring, which is a monocyclic aromatic ring of 5 or 6 ring atoms, containing one or two ring heteroatoms of N, O or S, with the remaining ring atoms being carbon, and
(3) a heterocyclyl ring, which is a non-aromatic monocyclic ring of 5 or 6 ring atoms, containing one or two ring heteroatoms of N or $S(O)_n$ (where n is an integer from 0 to 2), with the remaining ring atoms being carbon, wherein one of the ring carbon atoms of the heterocyclyl ring is optionally replaced with a carbonyl group;

$R^1$ and $R^{1''}$ are independently selected from the group consisting of:
(1) hydrogen,
(2) halogen,
(3) nitro, (4) cyano,
(5) amino,
(6) C$_{1-6}$ alkyl,
(7) heteroalkyl,
(8) C$_{3-7}$ cycloalkyl,
(9) C$_{2-6}$ alkenyl,
(10) C$_{2-6}$ alkynyl,
(11) hydroxy,
(12) C$_{1-6}$ alkoxy,
(13) —NR'R" or —(C$_{0-6}$ alkylene)-NR'R", in which R' and R" are independently selected from the group consisting of hydrogen, C$_{1-6}$ alkyl, heteroalkyl, formyl, C$_{1-6}$ alkylcarbonyl, optionally substituted C$_{3-7}$ cycloalkylcarbonyl, optionally substituted arylcarbonyl, optionally substituted heteroarylcarbonyl, optionally substituted heterocyclylcarbonyl, C$_{1-6}$ alkylsulfonyl, optionally substituted C$_{3-7}$ cycloalkylsulfonyl, optionally substituted arylsulfonyl, optionally substituted heteroarylsulfonyl, and optionally substituted heterocyclylsulfonyl, and
(14) —(C$_{0-6}$ alkylene)-O', in which R' is hydrogen, C$_{1-6}$ alkyl, heteroalkyl, formyl or C$_{1-6}$ alkylcarbonyl,
wherein both R$^1$ and R$^{1'}$ exist or alternatively R$^1$ exists but R$^{1'}$ does not exist;

R$^2$, R$^{2'}$ and R$^{2''}$ are independently selected from the group consisting of hydrogen, halogen, cyano, nitro, amino, mono-C$_{1-6}$ alkyl substituted amino, di-C$_{1-6}$ alkyl substituted amino, C$_{1-6}$ alkyl, C$_{2-6}$ alkenyl, C$_{2-6}$ alkynyl, heteroalkyl, hydroxy, and C$_{1-6}$ alkoxy;

X is phenylene optionally substituted by one, two or three substituents independently selected from the group consisting of halogen, cyano, nitro, amino, mono-C$_{1-6}$ alkyl substituted amino, di-C$_{1-6}$ alkyl substituted amino, C$_{1-6}$ alkyl, C$_{2-6}$ alkenyl, C$_{2-6}$ alkynyl, heteroalkyl, hydroxy, C$_{1-6}$ alkoxy, halo C$_{1-6}$ alkyl, halo C$_{1-6}$ alkoxy, heteroalkyloxy, C$_{1-6}$ alkylsulfonyl, C$_{1-6}$ alkylsulfinyl, C$_{1-6}$ alkylthio, C$_{1-6}$ alkylsulfonyl-C$_{1-6}$ alkyl, C$_{1-6}$ alkylsulfinyl-C$_{1-6}$ alkyl, C$_{1-6}$ alkylthio-C$_{1-6}$ alkyl, acyl, formyl, C$_{1-6}$ alkoxycarbonyl, halo C$_{1-6}$ alkoxycarbonyl, heteroalkyloxycarbonyl and heteroalkylcarbonyl; and Y is selected from the group consisting of:
(1) an optionally substituted heteroaryl, wherein the heteroaryl is a monocyclic aromatic radical of 6 ring atoms, containing one or two ring heteroatoms of N(O)n (where n is 0 or 1), O, or S, with the remaining ring atoms being carbon atoms, and
(2) an optionally substituted heterocyclyl, wherein the heterocyclyl is a non-aromatic monocyclic radical of six ring atoms, containing one or two ring heteroatoms of N, O, or S(O)$_n$ (where n is an integer from 0 to 2), with the remaining ring atoms being carbon atoms.

While the broadest definition of A, R$^1$ to R$^{2'''}$, X and Y is described herein, certain radicals are preferred.

i) In the compound of formula (I), A is preferably a phenyl ring or heteroaryl ring. A heteroaryl ring as A is preferably a five membered ring.

ii) In the compound of formula (I),

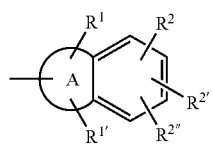

is preferably

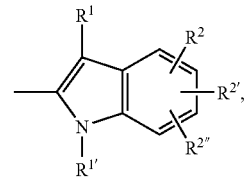 (a)

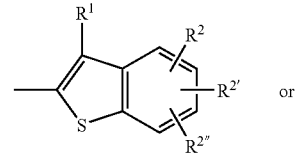 or (b)

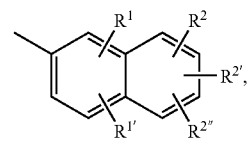 (c)

more preferably

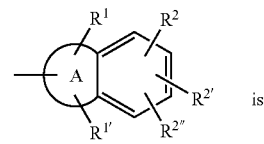 is

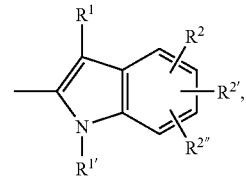 (a)

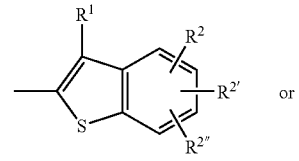 or (b)

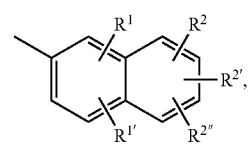 (c)

in which R$^1$ and R$^{1'}$ are independently hydrogen or C$_{1-6}$ alkyl, further more preferably

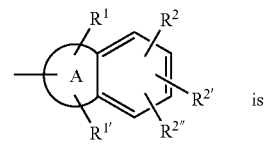 is

-continued

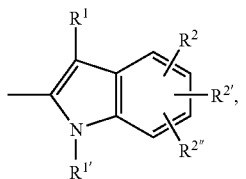
(a)

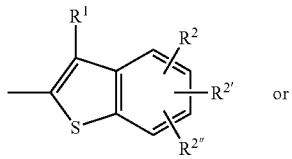
or
(b)

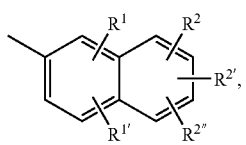
(c)

in which $R^2$, $R^{2'}$ and $R^{2''}$ are independently hydrogen or halogen.

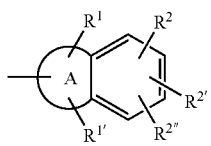

is especially

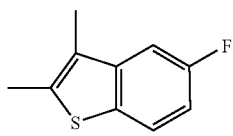
(b)

iii) In the compound of formula (I), Y is preferably at the para position of the phenylene group as X, with respect to the —NH—SO$_2$— group.

iv) In the compound of formula (I), X is preferably phenylene optionally substituted by one, two or three substituents independently selected from the group consisting of halogen, $C_{1-6}$ alkyl, $C_{1-6}$ alkoxy, halo $C_{1-6}$ alkyl, halo $C_{1-6}$ alkoxy, $C_{1-6}$ alkylsulfonyl, $C_{1-6}$ alkylsulfinyl, $C_{1-6}$ alkylthio, $C_{1-6}$ alkylsulfonyl-$C_{1-6}$ alkyl, $C_{1-6}$ alkylsulfinyl-$C_{1-6}$ alkyl, $C_{1-6}$ alkylthio $C_{1-6}$ alkyl and $C_{1-6}$ alkoxycarbonyl, more preferably X is phenylene substituted by halo $C_{1-6}$ alkyl or $C_{1-6}$ alkylsulfonyl at the ortho position with respect to the —NH—SO$_2$— group, further more preferably X is phenylene substituted by trifluoromethyl or methylsulfonyl at the ortho position with respect to the —NH—SO$_2$— group.

v) In the compound of formula (I), Y is preferably an optionally substituted heteroaryl, in which heteroaryl means a monocyclic aromatic radical of 6 ring atoms, containing one or two ring nitrogen atoms, with the remaining ring atoms being carbon atoms, or optionally substituted heterocyclyl, in which heterocyclyl means a non-aromatic mono-cyclic radical of six ring atoms, containing one or two ring nitrogen atoms, with the remaining ring atoms being carbon atoms. More preferably, Y is pyridyl, pyrimidinyl or piperidyl, optionally substituted by one or two substituents independently selected from the group consisting of halogen, $C_{1-6}$ alkoxy and $C_{1-6}$ alkoxycarbonyl.

vi) A preferred compound of the invention is a compound of formula (I), which is 5-fluoro-3-methyl-benzo[b]thiophene-2-sulfonic acid (4-pyridin-4-yl-2-trifluoromethyl-phenyl)-amide.

The compounds of the present invention can be prepared, for example, by the general synthetic procedures described below.

General Synthetic Procedures

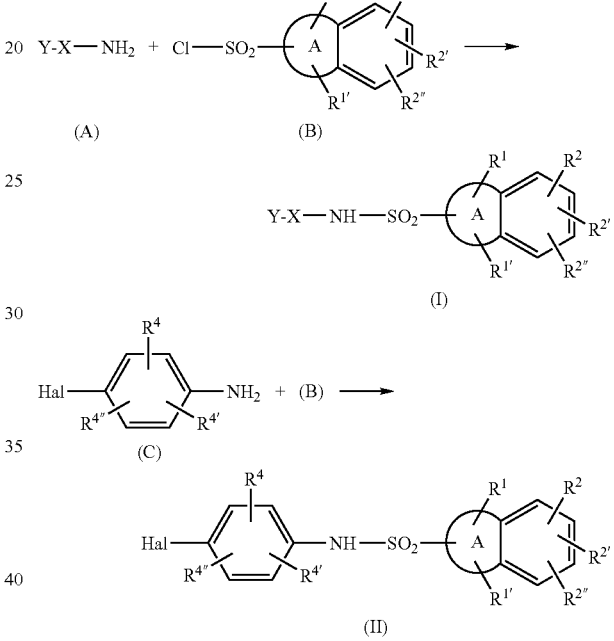

In scheme 1, A, $R^1$ to $R^{2''}$, X, Y and Hal are as defined before. $R^4$, $R^{4'}$ and $R^{4''}$ are independently hydrogen, halogen, cyano, nitro, amino, mono- or di-$C_{1-6}$ alkyl substituted amino, $C_{1-6}$ alkyl, $C_{2-6}$ alkenyl, $C_{2-6}$ alkynyl, heteroalkyl, hydroxy, $C_{1-6}$ alkoxy, halo $C_{1-6}$ alkyl, halo $C_{1-6}$ alkoxy, heteroalkyloxy, $C_{1-6}$ alkylsulfonyl, $C_{1-6}$ alkylsulfinyl, $C_{1-6}$ alkylthio, $C_{1-6}$ alkylsulfonyl-$C_{1-6}$ alkyl, $C_{1-6}$ alkylsulfinyl-$C_{1-6}$ alkyl, $C_{1-6}$ alkylthio $C_{1-6}$ alkyl, acyl, formyl, $C_{1-6}$ alkoxycarbonyl, halo $C_{1-6}$ alkoxycarbonyl, heteroalkyloxycarbonyl or heteroalkylcarbonyl.

The compounds of formula (I) and (II) are advantageously prepared by reacting sulfonyl chloride (B) with amine (A) or with an aniline (C) in the presence of a base. The base is preferably sodium hydride or an amine base selected from the group consisting of pyridine, picoline, triethylamine, diethylamine, diisopropylethylamine and 4-N-dimethylaminopyridine. The most preferred amines are pyridine and N,N-dimethylaminopyridine (DMAP). The solvents of choice are aprotic solvents with preferred ones selected from acetonitrile, dioxane, methylene chloride, tetrahydrofurane, toluene, dimethoxyethane, N,N-dimethylacetamide, dimethylsulfoxide, dimethylformamide and combinations thereof. The preferred temperature is in the range of 0° C. to 100° C.

Using compound (II) as an intermediate, compounds of formula (I) can be obtained by C—C bond forming reactions such as the Suzuki reaction, where the halide is reacted with a suitably substituted boronic acid derivative in the presence of a base and a palladium catalyst.

The sulfonyl chlorides (B) are either commercially available or can be synthesized by state-of-the-art methods from naphthalene or bicyclic heteroaromatic compounds or derivatives thereof. In particular, the sulfonyl chloride group can be introduced starting from an aryl lithium salt reacting with sulfur dioxide followed by oxidation/chlorination with for example sulfuryl chloride or N-chlorosuccinimide. Alternatively, an activated aromatic position can be reacted with chlorosulfonic acid or a sulfur trioxide complex such as $SO_3.DMF$ or $SO_3.pyridine$ followed by chlorination with e.g. thionyl chloride.

Aniline compounds (A) are either commercially available or can be synthesized by state-of-the-art methods. One option is to employ halogenated compound (C) in a C—C bond forming reactions such as the Suzuki reaction, where the halide is reacted with a suitably substituted boronic acid derivative in the presence of a base and a palladium catalyst. Halogenated aniline derivatives (C) are either commercially available or can be synthesized by state-of-the-art methods.

As described above, the compounds of formula (I) are active compounds and inhibit chymase. These compounds consequently prevent the activation of Angiotensin II, Endothelin, TGFb, Il1, SCF, collagenase and degradation of proteins like Thrombin, FN, APO A1,2. They therefore can be used for the treatment and/or prevention of allergic, inflammatory and/or fibrotic diseases, such as allergy, asthma, peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, atherothrombosis and/or burns/ulcers in Diabetes/CLI.

Prevention and/or treatment of allergic, inflammatory or fibrotic diseases, particularly atherothrombosis or asthma, is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of allergic, inflammatory and/or fibrotic diseases, particularly as therapeutically active substances for the treatment and/or prophylaxis of allergy, asthma, peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, atherothrombosis and/or burns/ulcers in Diabetes/CLI.

The invention also relates to the use of compounds as described above for the preparation of medicaments for the therapeutic and/or prophylactic treatment of allergic, inflammatory and/or fibrotic diseases, particularly for the therapeutic and/or prophylactic treatment of allergy, asthma, peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, atherothrombosis and/or burns/ulcers in Diabetes/CLI. Such medicaments comprise a compound as described above.

The invention also relates to the process and the intermediates for manufacturing the compounds of formula (I) as well as the process for manufacturing the intermediates.

The inhibition of chymase by the compounds of the present invention can be demonstrated by the peptide substrate assay as described hereinafter.

For the chymase a substrate was chosen containing the 4 amino acid peptide AAPF as a standard substrate for chymotrypsin like compounds (succinyl-Ala-Ala-Pro-Phe-[7-amino-4-methylcoumarin]; Lockhart B E, et al., "Recombinant human mast-cell chymase: an improved procedure for expression in *Pichia pastoris* and purification of the highly active enzyme." *Biotechnol Appl Biochem*. published as immediate publication 26 May 2004 as manuscript BA20040074)). The peptide was synthesized with a purity of 95% from Bachem, Bubendorf, Switzerland). Chymase purified from human skin mast cells was obtained from Calbiochem (Merck Biosciences, San Diego, Calif., USA). The assay buffer was 0.15 M NaCl, 0.05M, Tris HCl, 0.05% CHAPS (3-[(3-Cholamidopropyl)-dimethylammonio]-1-propane sulphonate), 0.1 mg/ml Heparin (Heparin sodium, Sigma, porcine intestinal mucosa), 0.02 mM AAPF-substrate, 1 nM Chymase at pH 7.4. The assay was performed in 96-well plates (Packard Optiplate), with a 0.05 ml volume at room temperature. Chymase activity was indicated by the initial rate of increase in fluorescence at 340/440 nm (excitation/emission) from free 7-amino-4-methylcoumarin released from the substrate. Inhibition of the activity by inhibitory compounds was read after 30 min pre-incubation with the chymase at room temperature in assay buffer without AAPF-substrate. The assay was then started by addition of the indicated concentration of AAPF-substrate.

The IC50 values of the active compounds of the present invention preferably amount to about 1000 to 1 nM, especially about 30 to 1 nM.

| Example | IC50 (nM) |
| --- | --- |
| Example 2 | 35 |
| Example 16 | 106 |
| Example 21 | 3 |

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

EXAMPLES

The following Examples serve to illustrate the present invention in more detail. They are, however, not intended to limit its scope in any manner.

Example 1

5-Fluoro-3-methyl-benzo[b]thiophene-2-sulfonic acid(4-bromo-2-trifluoromethyl-phenyl)-amide

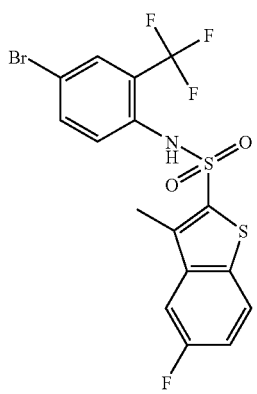

To an ice cooled solution of 4-bromo-2-(trifluoromethyl)benzenamine (CAS 445-02-3, 18 g) in pyridine (25 ml) was added 5-fluoro-3-methylbenzo[b]thiophene-2-sulphonyl chloride (CAS:404964-34-7, 2.0 g). The reaction mixture was stirred at rt for 72 h, concentrated under vacuum, and the residue was chromatographed over silica gel using heptane/chloroform as eluent to obtain 5-fluoro-3-methyl-benzo[b]thiophene-2-sulfonic acid(4-bromo-2-trifluoromethyl-phenyl)-amide (2.35 g) as a colorless solid. MS (ISN): 465.9, 468.0 (M−H)−

Example 2

5-Fluoro-3-methyl-benzo[b]thiophene-2-sulfonic acid(4-pyridin-4-yl-2-trifluoromethyl-phenyl)-amide

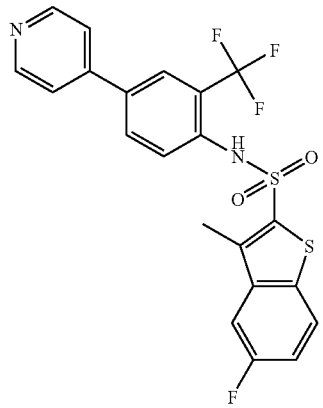

A suspension of 5-fluoro-3-methyl-benzo[b]thiophene-2-sulfonic acid(4-bromo-2-trifluoromethyl-phenyl)-amide (0.5 g) and 4-pyridineboronic acid (0.197 g) in 1,2-dimethoxyethane (6 ml), ethanol (2 ml) and 2 M aqueous sodium carbonate solution (4.0 ml) was degassed 3-4 times to remove oxygen, then tetrakis(triphenylphosphine)palladium (0.065 g) was added. The reaction mixture was stirred at 80° C. for 3 h, quenched with ice/water, and extracted with ethyl acetate. The organic layers were washed, dried and concentrated. The residue was chromatographed over silica gel using heptane/ethyl acetate as eluent to obtain the title compound (0.35 g) as a yellowish solid. MS (ISP): 467.3 (M+H)+

Example 3

5-Fluoro-3-methyl-benzo[b]thiophene-2-sulfonic acid[4-(2,6-difluoro-pyridin-4-yl)-2-trifluoromethyl-phenyl]-amide

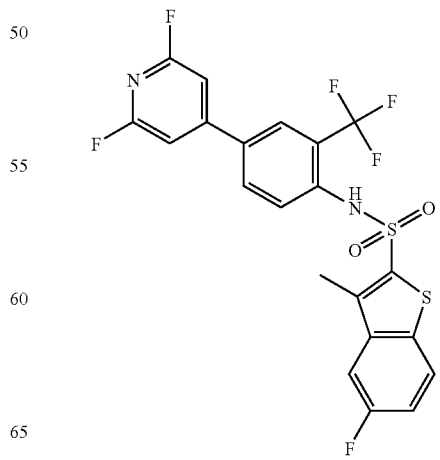

This compound was prepared in analogy to Example 2 starting from 5-fluoro-3-methyl-benzo[b]thiophene-2-sulfonic acid(4-bromo-2-trifluoromethyl-phenyl)-amide (0.12 g) and 2,6-difluoropyridine-4-boronic acid (0.063 g) in 1,2-dimethoxyethane (1.5 ml), ethanol (0.32 ml) and 2 M aqueous sodium carbonate solution (1.0 ml) with tetrakis(triphenylphosphine)palladium (0.055 g) to obtain the title compound (0.055 g) as a brownish solid. MS (ISP): 520.2 (M+NH4)+

Example 4

5-Fluoro-3-methyl-benzo[b]thiophene-2-sulfonic acid[4-(3-fluoro-pyridin-4-yl)-2-trifluoromethyl-phenyl]-amide

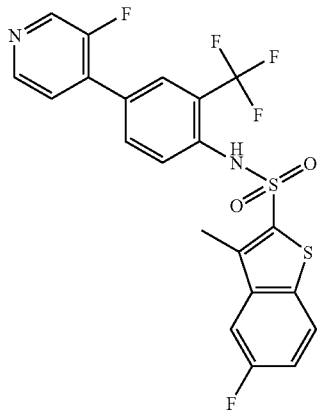

This compound was prepared in analogy to Example 2 starting from 5-fluoro-3-methyl-benzo[b]thiophene-2-sulfonic acid(4-bromo-2-trifluoromethyl-phenyl)-amide (0.12 g) and 3-fluoropyridine-4-boronic acid hydrate (0.061 g) in 1,2-dimethoxyethane (1.5 ml), ethanol (0.32 ml) and 2 M aqueous sodium carbonate solution (1.0 ml) with tetrakis (triphenylphosphine)palladium (0.050 g) to obtain the title compound (0.025 g) as a yellowish foam. MS (ISP): 485.3 (M+H)+

Example 5

5-Fluoro-3-methyl-benzo[b]thiophene-2-sulfonic acid[4-(2-fluoro-pyridin-4-yl)-2-trifluoromethyl-phenyl]-amide

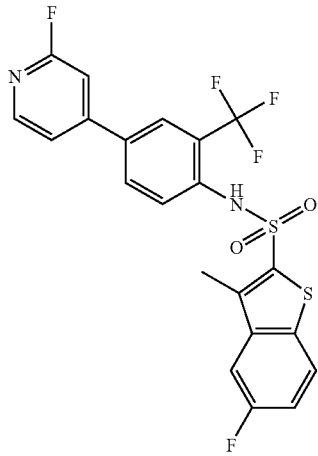

This compound was prepared in analogy to Example 2 starting from 5-fluoro-3-methyl-benzo[b]thiophene-2-sulfonic acid(4-bromo-2-trifluoromethyl-phenyl)-amide (0.12 g) and 2-fluoropyridine-4-boronic acid (0.072 g) in 1,2-dimethoxyethane (1.5 ml), ethanol (0.32 ml) and 2 M aqueous sodium carbonate solution (1.0 ml) with tetrakis(triphenylphosphine)palladium (0.065 g) to obtain the title compound (0.085 g) as a colorless foam. MS (ISN): 483.4 (M–H)−

Example 6

5-Fluoro-3-methyl-benzo[b]thiophene-2-sulfonic acid(4-pyridin-3-yl-2-trifluoromethyl-phenyl)-amide

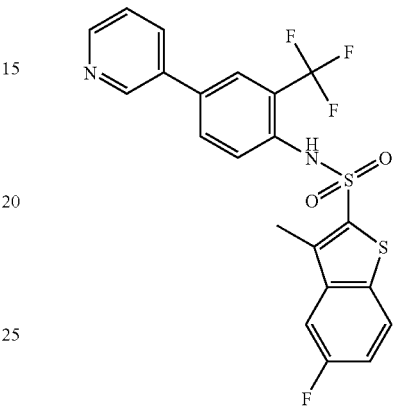

This compound was prepared in analogy to Example 2 starting from 5-fluoro-3-methyl-benzo[b]thiophene-2-sulfonic acid(4-bromo-2-trifluoromethyl-phenyl)-amide (0.10 g) and 3-pyridineboronic acid (0.052 g) in 1,2-dimethoxyethane (1.5 ml), ethanol (0.32 ml) and 2 M aqueous sodium carbonate solution (0.8 ml) with tetrakis(triphenylphosphine) palladium (0.050 g) to obtain the title compound (0.086 g) as a colorless solid. MS (ISP): 467.0 (M+H)+

Example 7

5-Fluoro-3-methyl-benzo[b]thiophene-2-sulfonic acid[4-(6-methoxy-pyridin-3-yl)-2-trifluoromethyl-phenyl]-amide

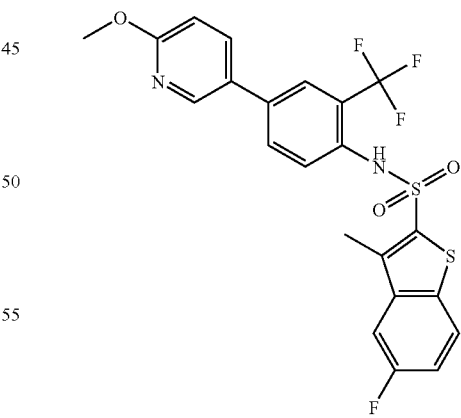

This compound was prepared in analogy to Example 2 starting from 5-fluoro-3-methyl-benzo[b]thiophene-2-sulfonic acid(4-bromo-2-trifluoromethyl-phenyl)-amide (0.10 g) and 2-methoxy-5-pyridineboronic acid (0.065 g) in 1,2-dimethoxyethane (1.5 ml), ethanol (0.32 ml) and 2 M aqueous sodium carbonate solution (0.8 ml) with tetrakis(triphenylphosphine)palladium (0.012 g) to obtain the title compound (0.081 g) as a colorless solid. MS (ISP): 497.3 (M+H)+

Example 8

5-Fluoro-3-methyl-benzo[b]thiophene-2-sulfonic acid(4-pyrimidin-5-yl-2-trifluoromethyl-phenyl)-amide

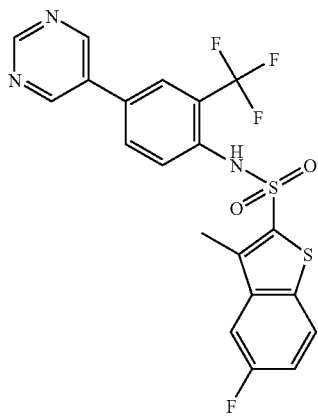

This compound was prepared in analogy to Example 2 starting from 5-fluoro-3-methyl-benzo[b]thiophene-2-sulfonic acid(4-bromo-2-trifluoromethyl-phenyl)-amide (0.10 g) and pyrimidine-5-boronic acid (0.053 g) in 1,2-dimethoxyethane (1.5 ml), ethanol (0.32 ml) and 2 M aqueous sodium carbonate solution (0.8 ml) with tetrakis(triphenylphosphine)palladium (0.012 g) to obtain the title compound (0.045 g) as a colorless solid. MS (ISN): 466.1 (M−H)⁻

Example 9

5-Fluoro-3-methyl-benzo[b]thiophene-2-sulfonic acid[4-(2-methoxy-pyrimidin-5-yl)-2-trifluoromethyl-phenyl]-amide

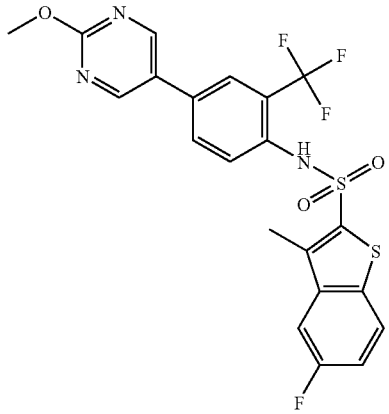

This compound was prepared in analogy to Example 2 starting from 5-fluoro-3-methyl-benzo[b]thiophene-2-sulfonic acid(4-bromo-2-trifluoromethyl-phenyl)-amide (0.10 g) and 2-methoxy-5-pyrimidineboronic acid (0.066 g) in 1,2-dimethoxyethane (1.5 ml), ethanol (0.32 ml) and 2 M aqueous sodium carbonate solution (1.0 ml) with tetrakis(triphenylphosphine)palladium (0.012 g) to obtain the title compound (0.064 g) as a colorless solid. MS (ISP): 498.4 (M+H)⁺

Example 10

5-Fluoro-3-methyl-benzo[b]thiophene-2-sulfonic acid[4-(5-fluoro-pyridin-3-yl)-2-trifluoromethyl-phenyl]-amide

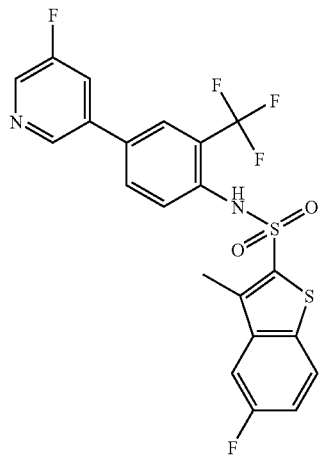

This compound was prepared in analogy to Example 2 starting from 5-fluoro-3-methyl-benzo[b]thiophene-2-sulfonic acid(4-bromo-2-trifluoromethyl-phenyl)-amide (0.12 g) and 5-fluoropyridine-3-boronic acid (0.072 g) in 1,2-dimethoxyethane (1.5 ml), ethanol (0.32 ml) and 2 M aqueous sodium carbonate solution (1.0 ml) with tetrakis(triphenylphosphine)palladium (0.015 g) to obtain the title compound (0.065 g) as a colorless solid. MS (ISP): 485.3 (M+H)⁺

Example 11

5-Fluoro-3-methyl-benzo[b]thiophene-2-sulfonic acid[4-(6-fluoro-pyridin-3-yl)-2-trifluoromethyl-phenyl]-amide

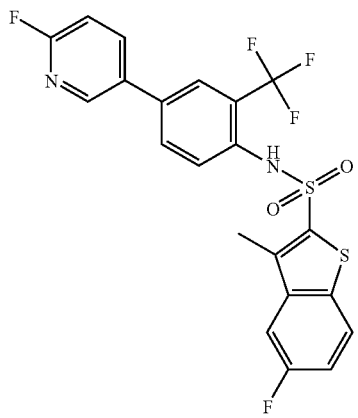

This compound was prepared in analogy to Example 2 starting from 5-fluoro-3-methyl-benzo[b]thiophene-2-sulfonic acid(4-bromo-2-trifluoromethyl-phenyl)-amide (0.12 g) and 2-fluoropyridine-5-boronic acid (0.072 g) in 1,2-dimethoxyethane (1.5 ml), ethanol (0.32 ml) and 2 M aqueous sodium carbonate solution (1.0 ml) with tetrakis(triphenylphosphine)palladium (0.015 g) to obtain the title compound (0.070 g) as a colorless solid. MS (ISP): 485.3 (M+H)⁺

Example 12

5-Fluoro-3-methyl-benzo[b]thiophene-2-sulfonic acid[4-(1-oxy-pyridin-4-yl)-2-trifluoromethyl-phenyl]-amide

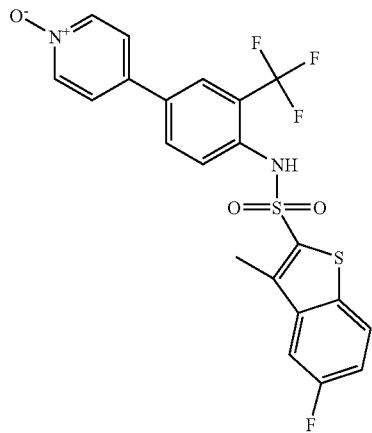

To a solution of 5-fluoro-3-methyl-benzo[b]thiophene-2-sulfonic acid(4-pyridin-4-yl-2-trifluoromethyl-phenyl)-amide (cf. Example 2, 0.27 g) in chloroform (5.0 ml) was added m-chloroperbenzoic acid 85% (0.195 g). The reaction mixture was stirred at rt for 4 h and washed with bicarbonate solution. The organic phase was dried over magnesium sulphate and concentrated. The residue was chromatographed on a silica gel column (10 g) using dichloromethane/methanol as eluent to obtain the title compound (0.065 g) as yellow foam. MS (ISP): 483.4 (M+H)$^+$

Example 13

5-Fluoro-3-methyl-benzo[b]thiophene-2-sulfonic acid(2-methylsulfanylmethyl-4-pyridin-4-yl-phenyl)-amide

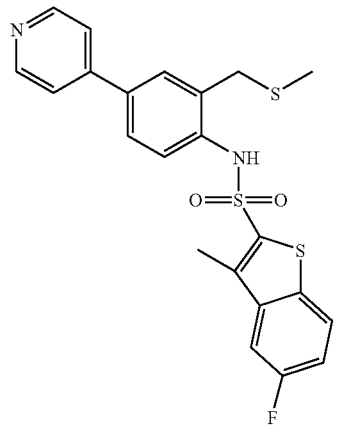

a) 5-Fluoro-3-methyl-benzo[b]thiophene-2-sulfonic acid(4-bromo-2-methylsulfanylmethyl-phenyl)-amide

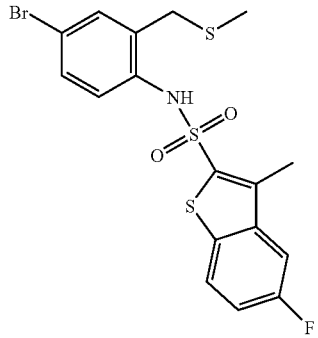

This compound was prepared in analogy to Example 1 starting from 4-bromo-2-methylsulfanylmethyl-phenylamine (Allen, David George; Eldred, Colin David; Judkins, Brian David; Mitchell, William Leonard, WO 9749699, 4.6 g) and 5-fluoro-3-methylbenzo[b]thiophene-2-sulphonyl chloride (1.06 g) to obtain the desired compound (1.3 g) as a brownish solid. MS (ISN): 458.1, 460.0 (M−H)$^-$ b) 5-Fluoro-3-methyl-benzo[b]thiophene-2-sulfonic acid(2-methylsulfanylmethyl-4-pyridin-4-yl-phenyl)-amide This compound was prepared in analogy to Example 2 starting from 5-fluoro-3-methyl-benzo[b]thiophene-2-sulfonic acid(4-bromo-2-methylsulfanylmethyl-phenyl)-amide (0.23 g) and 4-pyridineboronic acid (0.092 g) in 1,2-dimethoxyethane (10 ml), ethanol (2 ml) and 2 M aqueous sodium carbonate solution (2 ml) with tetrakis(triphenylphosphine)palladium (0.058 g) to obtain the title compound (0.153 g) as a brownish foam (0.153 g). MS (ISN): 457.2 (M−H)$^-$

Example 14

5-Fluoro-3-methyl-benzo[b]thiophene-2-sulfonic acid(2-methanesulfinylmethyl-4-pyridin-4-yl-phenyl)-amide

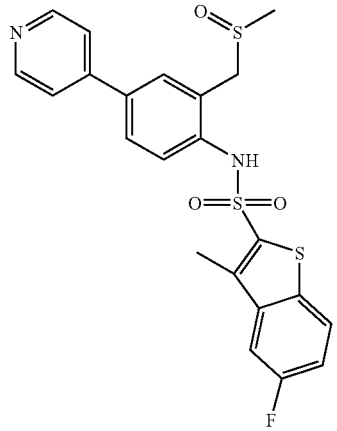

a) 5-Fluoro-3-methyl-benzo[b]thiophene-2-sulfonic acid(4-bromo-2-methanesulfinylmethyl-phenyl)-amide

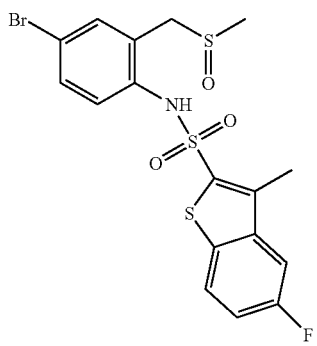

To a solution of 5-fluoro-3-methyl-benzo[b]thiophene-2-sulfonic acid(4-bromo-2-methylsulfanylmethyl-phenyl)-amide (0.46 g) (cf. example 13a) in chloroform (25 ml) was added m-chloroperbenzoic acid 85% (0.272 g). The reaction mixture was stirred at rt for 18 h, concentrated, and the crude residue was chromatographed on silica gel using heptane/ethyl acetate as eluent to obtain the desired compound (0.31 g) as an off-white solid. MS (ISN): 473.9, 476.0 (M−H)⁻ b) 5-Fluoro-3-methyl-benzo[b]thiophene-2-sulfonic acid(4-bromo-2-methanesulfinylmethyl-phenyl)-amide

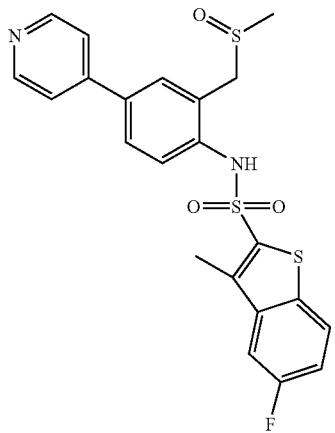

This compound was prepared in analogy to Example 2 starting from 5-fluoro-3-methyl-benzo[b]thiophene-2-sulfonic acid(4-bromo-2-methanesulfinylmethyl-phenyl)-amide (0.238 g) and 4-pyridineboronic acid (0.092 g) in 1,2-dimethoxyethane (10 ml), ethanol (2 ml) and 2 M aqueous sodium carbonate solution (2 ml) with tetrakis(triphenylphosphine)palladium (0.058 g) to obtain the title compound (0.077 g) as a yellowish foam. MS (ISN): 473.3 (M−H)⁻

Example 15

5-Fluoro-3-methyl-benzo[b]thiophene-2-sulfonic acid(2-methanesulfonylmethyl-4-pyridin-4-yl-phenyl)-amide

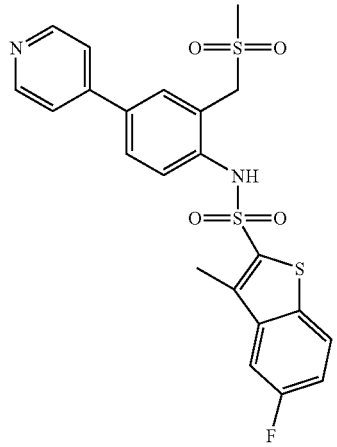

a) 5-Fluoro-3-methyl-benzo[b]thiophene-2-sulfonic acid(4-bromo-2-methanesulfonylmethyl-phenyl)-amide

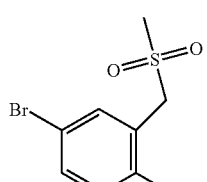

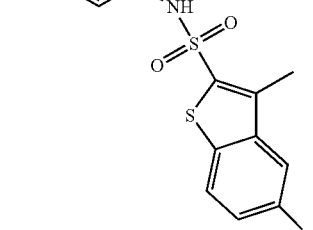

To a solution of 5-fluoro-3-methyl-benzo[b]thiophene-2-sulfonic acid(4-bromo-2-methylsulfanylmethyl-phenyl)-amide (0.46 g) (cf. Example 13a) in chloroform (25 ml) was added 85% m-chloroperbenzoic acid (0.272 g). The reaction mixture was stirred at rt for 18 h, concentrated, and the crude residue was chromatographed on silica gel using heptane/ethyl acetate as eluent to obtain the desired compound (0.138 g) as a brownish solid. MS (ISN): 490.0, 492.0 (M−H)⁻

5-Fluoro-3-methyl-benzo[b]thiophene-2-sulfonic acid(2-methanesulfonylmethyl-4-pyridin-4-yl-phenyl)-amide This compound was prepared in analogy to Example 2 starting from 5-fluoro-3-methyl-benzo[b]thiophene-2-sulfonic acid(4-bromo-2-methanesulfonylmethyl-phenyl)-amide (0.123 g) and 4-pyridineboronic acid (0.0462 g) in 1,2-dimethoxyethane (5 ml), ethanol (1 ml) and 2 M aqueous sodium carbonate solution (2 ml) with tetrakis(triphenylphosphine)palladium (0.035 g) to obtain the title compound (0.029 g) as a yellowish foam. MS (ISN): 489.1 (M−H)⁻

Example 16

5-Fluoro-3-methyl-benzo[b]thiophene-2-sulfonic acid(2-ethyl-4-pyridin-4-yl-phenyl)-amide

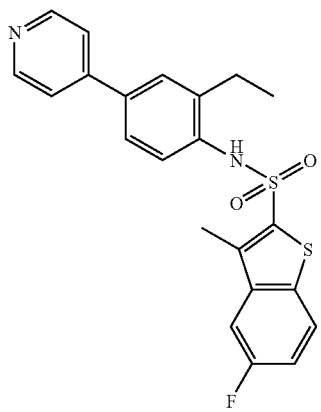

a) 5-Fluoro-3-methyl-benzo[b]thiophene-2-sulfonic acid(4-bromo-2-ethyl-phenyl)-amide

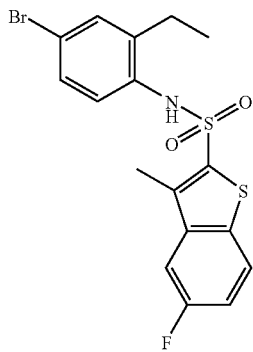

This compound was prepared in analogy to Example 1, starting from 4-bromo-2-ethylaniline (CAS:45762-41-2, 2.0 g) and 5-fluoro-3-methylbenzo[b]thiophene-2-sulphonyl chloride (0.265 g) in pyridine (2.0 ml) for 4 h to obtain the desired compound (0.20 g) as a colorless solid. MS (ISP): 445.0, 447.0 (M+NH4)$^+$ b) 5-Fluoro-3-methyl-benzo[b]thiophene-2-sulfonic acid(2-ethyl-4-pyridin-4-yl-phenyl)-amide This product was prepared in analogy to Example 2 starting from 5-fluoro-3-methyl-benzo[b]thiophene-2-sulfonic acid (4-bromo-2-ethyl-phenyl)-amide (0.10 g) and 4-pyridineboronic acid (0.043 g) in 1,2-dimethoxyethane (1.5 ml), ethanol (0.25 ml) and 2 M aqueous sodium carbonate solution (0.9 ml) with tetrakis(triphenylphosphine)palladium (0.013 g) to obtain the title compound (0.025 g) as a yellowish foam. MS (ISP): 427.3 (M+H)$^+$

Example 17

5-Fluoro-3-methyl-benzo[b]thiophene-2-sulfonic acid(4-bromo-2-trifluoromethoxy-phenyl)-amide

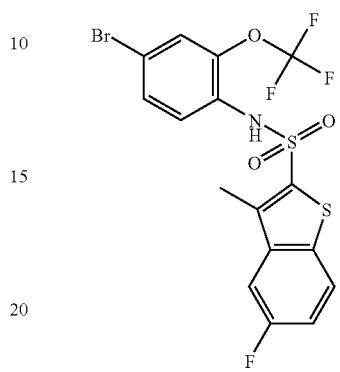

This compound was prepared in analogy to Example 1, starting from 4-bromo-2-(trifluoromethoxy)aniline (CAS: 175278-09-8, 2.82 g) and 5-fluoro-3-methylbenzo[b] thiophene-2-sulphonyl chloride (0.265 g) in pyridine (2.0 ml) for 18 h to obtain the desired compound (0.12 g) as a colorless foam. MS (ISP): 501.0, 503.0 (M+NH4)$^+$

Example 18

5-Fluoro-3-methyl-benzo[b]thiophene-2-sulfonic acid(4-pyridin-4-yl-2-trifluoromethoxy-phenyl)-amide

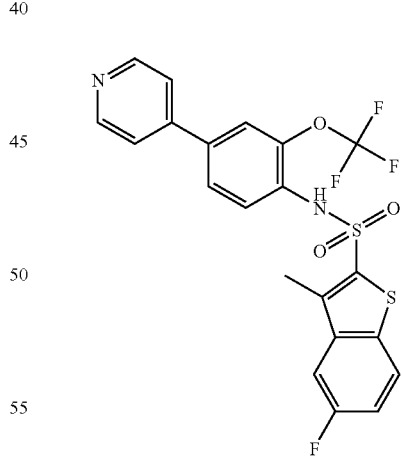

This compound was prepared in analogy to example 2 starting from 5-fluoro-3-methyl-benzo[b]thiophene-2-sulfonic acid(4-bromo-2-trifluoromethoxy-phenyl)-amide (0.075 g) and 4-pyridineboronic acid (0.029 g) in 1,2-dimethoxyethane (1.5 ml), ethanol (0.25 ml) and 2 M aqueous sodium carbonate solution (0.6 ml) with tetrakis(triphenylphosphine)palladium (0.009 g) to obtain the title compound (0.055 g) as a colorless solid. MS (ISP): 483.0 (M+H)$^+$

Example 19

5-Fluoro-3-methyl-benzo[b]thiophene-2-sulfonic acid(4-pyridin-4-yl-phenyl)-amide

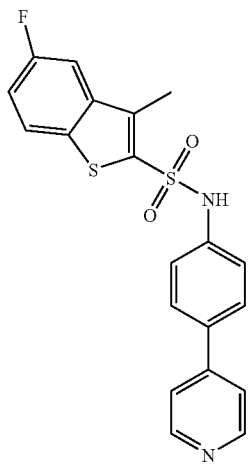

To a solution of (4-pyridine-4-yl)aniline (CAS: 13296-04-3, 0.290 g) in dichloromethane (12.0 ml) was added 5-fluoro-3-methylbenzo[b]thiophene-2-sulphonyl chloride (0.440 g) and DMAP (0.305 g). The reaction mixture was stirred at rt for 16 h, diluted with dichloromethane (12 ml) and chromatographed on silica gel using heptane/ethyl acetate as eluent to obtain the title compound (0.205 g) as an off-white solid. MS (ISN): 397.1 (M−H)−

Example 20

5-Fluoro-3-methyl-benzo[b]thiophene-2-sulfonic acid(2-methanesulfonyl-4-piperidin-4-yl-phenyl)-amide hydrochloride

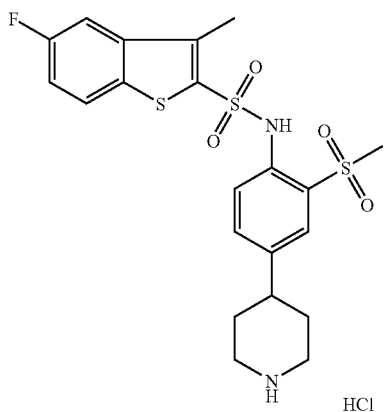

a) 4-(4-Chloro-3-methanesulfonyl-phenyl)-pyridine

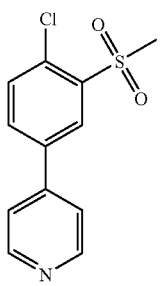

1-Bromo-4-chlorobenzene (12.25 g) was added portionwise to chlorosulfonic acid (56 g) at 5-10° C. The resulting mixture was heated to 130° C. for 16 h. After cooling, the mixture was added in a slow stream to well stirred ice/water (500 ml), and stirring was continued for a further 30 minutes. The colorless precipitate was collected by filtration. The wet filter cake was taken up in dichloromethane, separated from the water, and the organic phase was dried and evaporated to dryness (14.1 g). The dried mixture of 2 isomers was dissolved in THF (20 ml) and added to a solution of sodium sulfite (15.3 g) in water (100 ml). The reaction was exothermic, and the pH went down. Ice and conc. NaOH were added to keep the temperature at 20-30° C. and the pH at ca. 9. The reaction mixture was then stirred over night at rt and pH 9, acidified with conc. HCl to pH 1, and cooled down. The precipitate was filtered off, washed with cold water and dried over P2O5 under high vacuum over night to obtain a colorless sulfinic acid derivative (10.5 g). This acid was dissolved in DMF (100 ml), methyl iodide (13 g) was added, followed by potassium carbonate (14.0 g). The reaction mixture was stirred at rt overnight, and concentrated under high vacuum. To the residue was added water and extracted with tert-butyl-methyl ether. The organics were washed, dried and concentrated. The residue was chromatographed over silica gel using cyclohexane/ethyl acetate as eluent to produce the methylsulfonyl derivative (9.1 g) which was still a mixture of 2 isomers. This mixture (9.0 g) was dissolved in dimethoxyethane (400 ml) and ethanol (90 ml) and displaced with 2M aqueous sodium carbonate solution (200 ml). The reaction mixture was degassed a few times, and tetrakis(triphenylphosphine) palladium (3.0 g) was added. The mixture was heated to 80° C. for 16 h and concentrated to dryness. The residue was taken up in dichloromethane/water, extracted, dried and concentrated. The solid residue was taken up in ether, filtered, washed and dried to obtain the desired compound (5.54 g) as off-white crystals. MS (EI): 267.1 (M)

b) Benzyl-(2-methanesulfonyl-4-pyridin-4-yl-phenyl)-amine

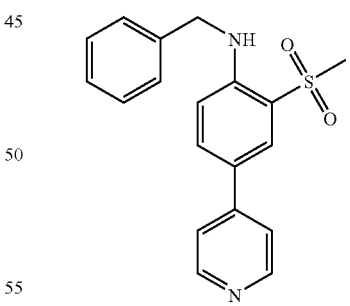

A suspension of 4-(4-chloro-3-methanesulfonyl-phenyl)-pyridin (5.5 g) in benzylamine (23 ml) was heated to 160° C. for 4 h, concentrated under high vacuum. The residue was quenched with ice/water and extracted with ethyl acetate. The organic layers were washed, dried and concentrated; the residue was chromatographed on silica gel with heptane/ethyl acetate. The compound containing fractions were evaporated, and the residue crystallized from methanol/ether to obtain the desired compound (5.75 g) as an off-white solid. MS (ISP): 339.1 (M+H)+ c) 2-Methanesulfonyl-4-pyridin-4-yl-phenylamine

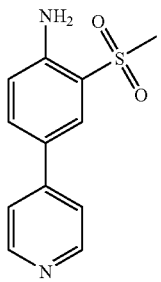

To a solution of benzyl-(2-methanesulfonyl-4-pyridin-4-yl-phenyl)-amine (2.0 g) in dioxane/methanol 1:1 (100 ml) was added 2N HCl (5 ml) and palladium black (1.0 g). The reaction mixture was hydrogenated at 1.1 bar and rt for 18 h. The catalyst was filtered off over a microfilter and washed with methanol. The filtrate was evaporated to dryness to obtain the desired compound (1.45 g) as a yellowish solid. MS (ISP): 249.1 (M+H)$^+$ d) 2-Methanesulfonyl-4-piperidin-4-yl-phenylamine

Compound with Acetic Acid

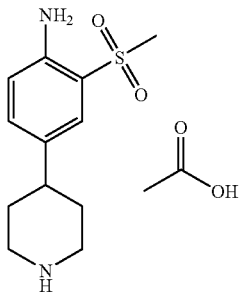

A suspension of 2-methanesulfonyl-4-pyridin-4-yl-phenylamine (0.70 g) and platinum oxide (0.70 g) in acetic acid (15 ml) was hydrogenated at 1.1 bar and 80° C. for 8 h. The reaction mixture was cooled to rt, filtered over a microfilter, washed with acetic acid, and concentrated to dryness to obtain the title compound (0.89 g) as a light yellow amorphous powder. MS (ISP): 255.4 (M+H)$^+$ e) 4-(4-Amino-3-methanesulfonyl-phenyl)-piperidine-1-carboxylic acid tert-butyl ester

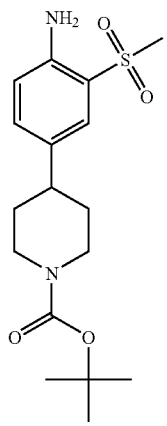

To a solution of 2-methanesulfonyl-4-piperidin-4-yl-phenylamine; compound with acetic acid (1.5 g) in dichloromethane (30 ml) was added di-tert-butylcarbonate (1.15 g) and saturated aqueous sodium carbonate solution (10 ml). The reaction mixture was stirred at rt for 3 h and extracted with dichloromethane. The organic phases were dried and concentrated, and the residue was chromatographed on silica gel using heptane/ethyl acetate as eluent to obtain the desired compound (0.64 g) as an off-white solid. MS (ISP): 355.1 (M+H)$^+$ f) 4-[4-(5-Fluoro-3-methyl-benzo[b]thiophene-2-sulfonylamino)-3-methanesulfonyl-phenyl]-piperidine-1-carboxylic acid tert-butyl ester

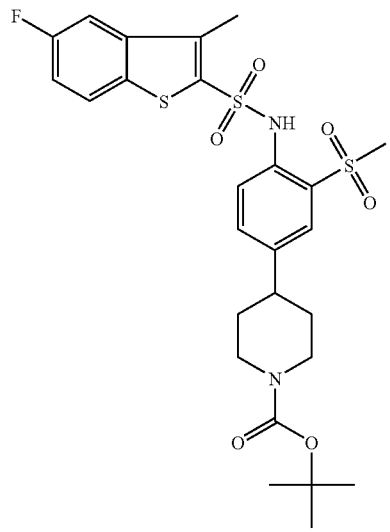

To an ice cooled suspension of sodium hydride (60-65% in mineral oil, 0.030 g) in absolute DMSO (3 ml) was added 4-(4-amino-3-methanesulfonyl-phenyl)-piperidine-1-carboxylic acid tert-butyl ester (0.106 g). The mixture was stirred at 0-5° C. for 30 minutes, and a solution 5-fluoro-3-methylbenzo[b]thiophene-2-sulphonyl chloride (0.237 g) in absolute DMSO (1 ml) was added dropwise. The reaction mixture was stirred at rt for 5 h, quenched with ice/water/1 N HCl, and extracted with ethyl acetate. The organic phases were washed, dried and concentrated, and the residue was chromatographed over silica gel using heptane/ethyl acetate as eluent to obtain the desired compound (0.0.025 g) methylbenzo[b]thiophene-2-sulphonyl chloride (0.237 g) to obtain the desired compound (0.025 g) as a yellowish foam. MS (ISN): 581.3 (M−H)$^-$ g) 5-Fluoro-3-methyl-benzo[b]thiophene-2-sulfonic acid(2-methanesulfonyl-4-piperidin-4-yl-phenyl)-amide hydrochloride A solution of 4-[4-(5-fluoro-3-methyl-benzo[b]thiophene-2-sulfonylamino)-3-methanesulfonyl-phenyl]-piperidine-1-carboxylic acid tert-butyl ester (0.025 g) in ethyl acetate (1 ml) was treated with 2.5 N HCl/ethyl acetate (2 ml). The reaction mixture was stirred at rt for 2 h. Ether (20 ml) was added, the precipitate was filtered off, washed with ether and dried under high vacuum over P$_2$O$_5$ to obtain the title compound (0.020 g) as a yellowish powder. MS (ISP): 483.3 (M+H)$^+$

Example 21

5-Fluoro-3-methyl-benzo[b]thiophene-2-sulfonic acid(2-methanesulfonyl-4-piperidin-4-yl-phenyl)-amide

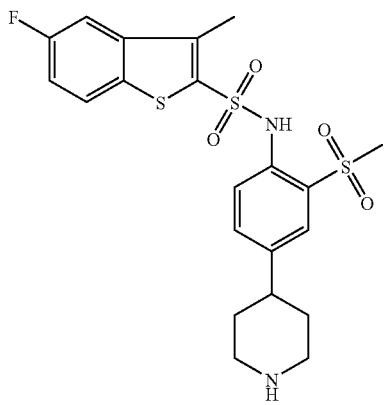

5-Fluoro-3-methyl-benzo[b]thiophene-2-sulfonic acid(2-methanesulfonyl-4-piperidin-4-yl-phenyl)-amide hydrochloride (cf. Example 20 g, 6 mg) was run through an HPLC-column with acetonitrile/water/formic acid to obtain the title compound (3 mg) as an off-white foam. MS (ISP): 483.3 (M+H)$^+$

Example 22

Naphthalene-2-sulfonic acid(2-methanesulfonyl-4-pyridin-4-yl-phenyl)-amide

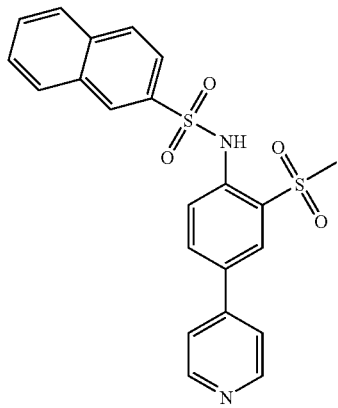

To a solution of 2-methanesulfonyl-4-pyridin-4-yl-phenylamine (cf. Example 20c, 0.046 g) in pyridine (0.5 ml) was added naphthalene-2-sulfochloride (0.051 g). The reaction mixture was stirred at 70° C. for 6 h, diluted with dichloromethane and chromatographed on silica gel using dichloromethane/methanol/ammonia to obtain the title compound (0.025 g) as an off-white solid. MS (ISP): 439.1 (M+H)$^+$

Example 23

5-Fluoro-3-methyl-benzo[b]thiophene-2-sulfonic acid(2-methanesulfonyl-4-pyridin-4-yl-phenyl)-amide

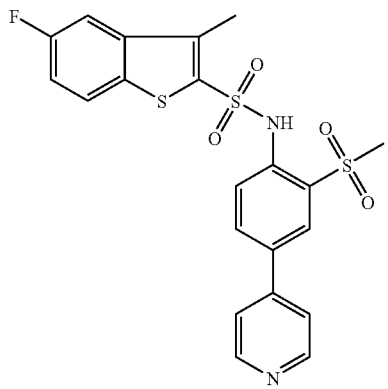

This compound was prepared in analogy to Example 20f starting from 2-methanesulfonyl-4-pyridin-4-yl-phenylamine (cf. Example 20c, 0.27 g) in tetrahydrofurane (10 ml) and 5-fluoro-3-methylbenzo[b]thiophene-2-sulphonyl chloride (0.265 g) with sodium hydride (0.10 g) at rt for 18 h to obtain the title compound (0.025 g) as a yellow foam. MS (ISN): 475.0 (M−H)$^−$

Example 24

4-[3-Methanesulfonyl-4-(1-methyl-1H-indole-2-sulfonylamino)-phenyl]-piperidine-1-carboxylic acid tert-butyl ester

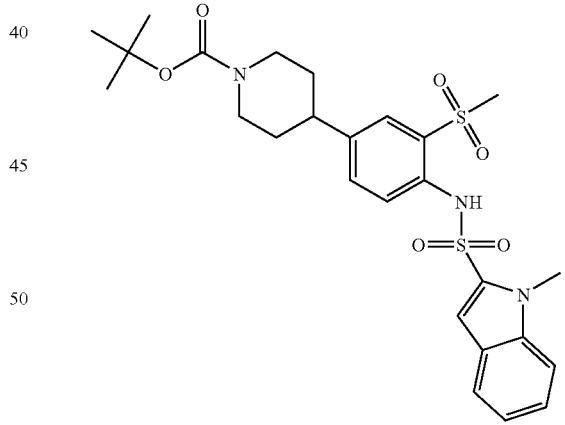

To a solution of 4-(4-amino-3-methanesulfonyl-phenyl)-piperidine-1-carboxylic acid tert-butyl ester (cf. Example 20e, 0.050 g) in dichloromethane (2.0 ml) was added 1-methyl-1H-indole-2-sulfonyl chloride (0.036 g; cf. Chan, Ming Fai; Wu, Chengde; Raju, Bore Gowda; Kogan, Timothy; Kois, Adam; Verner, Erik Joel; Castillo, Rosario Silvestre; Yalamorri, Venkatachalapathi; Balaji, Vitukudi Narayanaiyengar, U.S. Pat. No. 5,962,490) and DMAP (0.021 g). The reaction mixture was stirred at 80° C. for 18 h, cooled and directly chromatographed on silica gel using heptane/ethyl acetate as eluent to obtain the title compound (0.048 g) as a yellowish foam. MS (ISN): 546.5 (M−H)$^−$

Example 25

1-Methyl-1H-indole-2-sulfonic acid(2-methanesulfonyl-4-piperidin-4-yl-phenyl)-amide hydrochloride

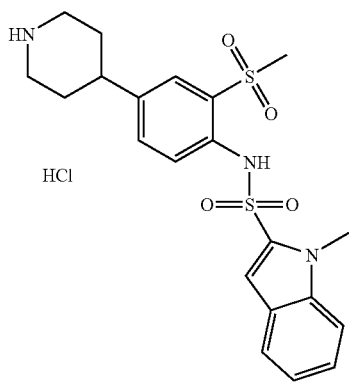

A solution of 4-[3-methanesulfonyl-4-(1-methyl-1H-indole-2-sulfonylamino)-phenyl]-piperidine-1-carboxylic acid tert-butyl ester (0.038 g) was treated with 2.5 N HCl/ethyl acetate (2.5 ml). The reaction mixture was stirred at rt for 2 h, then ether (20 ml) was added. The precipitate was collected, washed with ether and dried under high vacuum over $P_2O_5$ to produce the title compound (0.032 g) as an off-white powder. MS (ISN): 446.4 (M−H)⁻

Example 26

6-Fluoro-naphthalene-2-sulfonic acid(2-methanesulfonyl-4-pyridin-4-yl-phenyl)-amide

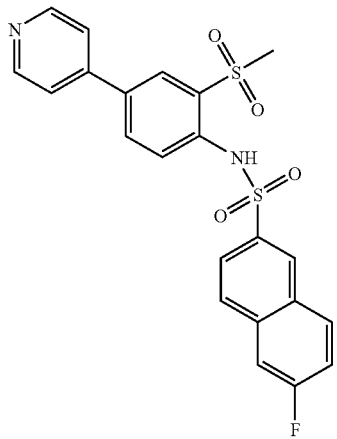

To a solution of 2-methanesulfonyl-4-pyridin-4-yl-phenylamine (cf. Example 20c, 0.27 g) and 6-fluoro-naphthalene-2-sulfonyl chloride (0.148 g; cf. Brown, George Robert; Stokes, Elaine Sophie Elisabeth; Waterson, David; Wood, Robin. WO 9706802) in dichloromethane (1.0 ml) was added DMAP (0.037 g). The reaction mixture was stirred at rt for 2 h and directly chromatographed on silica gel using heptane/ethyl acetate as eluent to produce the title compound (0.098 g) as a colorless foam. MS (ISP): 457.3 (M+H)⁺

Example 27

1H-Indole-2-sulfonic acid(4-pyridin-4-yl-phenyl)-amide hydrochloride

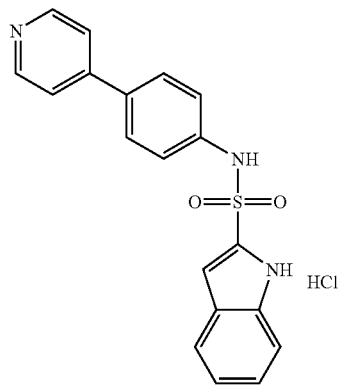

a) 2-(4-Pyridin-4-yl-phenylsulfamoyl)-indole-1-carboxylic acid tert-butyl ester

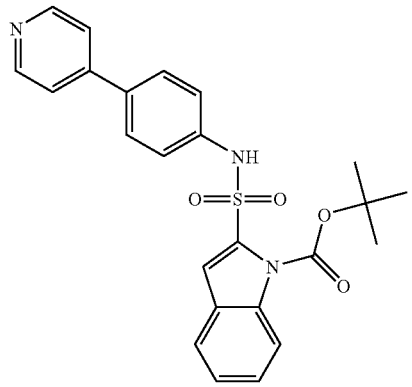

To a solution of (4-pyridine-4-yl)aniline (CAS: 13296-04-3, 0.054 g) and 2-chlorosulfonyl-indole-1-carboxylic acid tert-butyl ester (0.120 g; cf. Shankar, Bandarpalle B.; Gilbert, Eric; Rizvi, Razia K.; Huang, Chunli; Kozlowski, Joseph A.; McCombie, Stuart; Shih, Neng-Yang. WO 2006002133) in 1,2-dichlorethane (5.0 ml) was added DMAP (0.047 g). The reaction mixture was stirred at 50° C. for 3 h and chromatographed on silica gel using dichloromethane/ethyl acetate as eluent to obtain the desired compound (0.070 g) as a colorless powder. MS (ISP): 450.4 (M+H)⁺ b) 1H-Indole-2-sulfonic acid(4-pyridin-4-yl-phenyl)-amide hydrochloride

To a solution of 2-(4-pyridin-4-yl-phenylsulfamoyl)-indole-1-carboxylic acid tert-butyl ester (0.030 g) in ethyl acetate (1.0 ml) was added 3.5 N HCl/ethyl acetate (2.0 ml). The reaction mixture was stirred at 45° C. for 8 h, then diluted with ether (40 ml). The precipitate was collected, washed with ether and dried under high vacuum over $P_2O_5$ to obtain the title compound (0.025 g) as a colorless amorphous powder. MS (ISP): 350.4 (M+H)⁺

Example 28

5-Fluoro-1-methyl-1H-indole-2-sulfonic acid(2-methanesulfonyl-4-piperidin-4-yl-phenyl)-amide hydrochloride

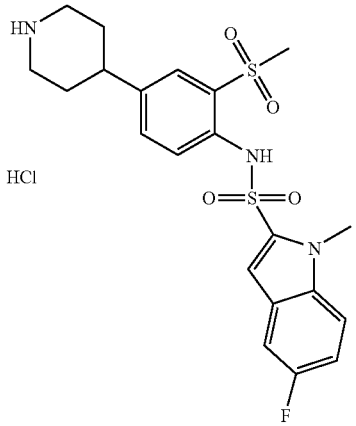

a) 5-Fluoro-1-methyl-1H-indole-2-sulfonyl chloride

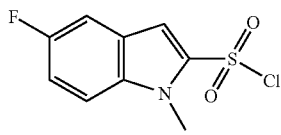

To a solution of 1-methyl-5-fluoroindole (CAS: 116176-92-2, 1.98 g) in absolute ether (100 ml) was added dropwise at −78° C. tert-BuLi (1.7 N in pentane, 12.4 ml). The reaction mixture was stirred at that temperature for 60 minutes, then sulfur dioxide was passed over the solvent surface until the exothermic reaction ceased. The mixture was further stirred for 30 minutes at rt and concentrated to dryness. The crude residue was suspended in dichloromethane (100 ml) and NCS (2.94 g) was added. The reaction mixture was stirred at rt for 4 h, quenched with ice/water, and extracted with dichloromethane. The organic phases were washed, dried and concentrated. The residue was chromatographed on silica gel using heptane/ethyl acetate as eluent to obtain the desired product (0.405 g) as a yellowish solid. MS (EI): 247.1 (M)

b) 4-[4-(5-Fluoro-1-methyl-1H-indole-2-sulfonylamino)-3-methanesulfonyl-phenyl]piperidine-1-carboxylic acid tert-butyl ester

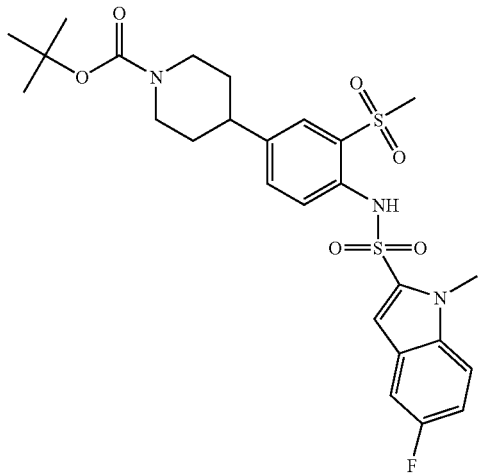

To a solution of 4-(4-amino-3-methanesulfonyl-phenyl)-piperidine-1-carboxylic acid tert-butyl ester (cf. Example 24e, 0.048 g) in 1,2-dichloroethane (3.0 ml) was added 5-fluoro-1-methyl-1H-indole-2-sulfonyl chloride (0.035 g) and DMAP (0.025 g). The reaction mixture was stirred at 80° C. for 72 h, diluted with dichloromethane (2 ml) and chromatographed on silica gel using dichloromethane/ethyl acetate as eluent to obtain the title compound (0.019 g) as an off-white foam. MS (ISN): 564.3 (M−H)⁻ c) 5-Fluoro-1-methyl-1H-indole-2-sulfonic acid(2-methanesulfonyl-4-piperidin-4-yl-phenyl)-amide hydrochloride

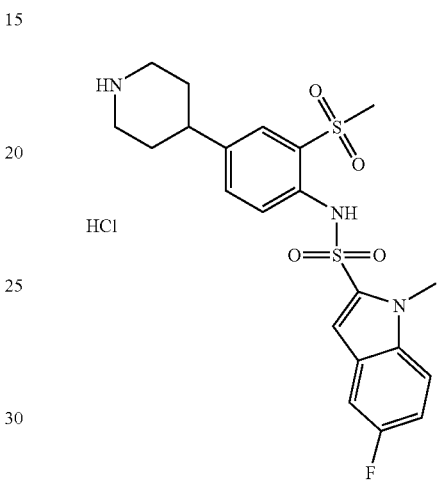

A solution of 4-[4-(5-fluoro-1-methyl-1H-indole-2-sulfonylamino)-3-methanesulfonyl-phenyl]-piperidine-1-carboxylic acid tert-butyl ester (0.019 g) was treated with 2.5 N HCl/ethyl acetate (2.5 ml). The reaction mixture was stirred at rt for 3 h, then ether (20 ml) was added. The precipitate was collected, washed with ether and dried under high vacuum over P₂O₅ to produce the title compound (0.014 g) as an off-white amorphous powder. MS (ISN): 464.0 (M−H)⁻

Example 29

5-Fluoro-3-methyl-1H-indole-2-sulfonic acid(4-pyridin-4-yl-2-trifluoromethyl-phenyl)-amide hydrochloride

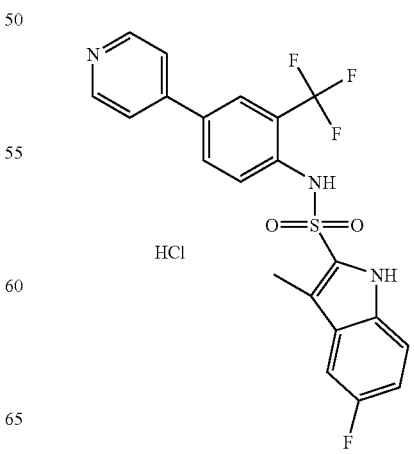

a) 5-Fluoro-3-methyl-indole-1-carboxylic acid tert-butyl ester

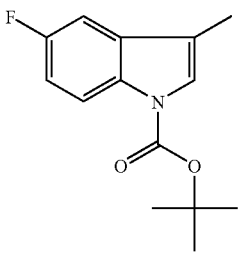

To a solution of 5-fluoro-3-methyl-indole (CAS: 392-13-2, 2.5 g) in THF (25 ml) were added at 0-5° C. di-tert-butyldicarbonate (4.02 g) and DMAP (0.205 g). The reaction mixture was stirred at rt for 4 h, concentrated, and the residue was chromatographed on silica gel using heptane/ethyl acetate as eluent to obtain the desired compound (3.15 g) as a colorless solid. MS (ISP): 250.1 (M+H)$^+$ b) 2-Chlorosulfonyl-5-fluoro-3-methyl-indole-1-carboxylic acid tert-butyl ester

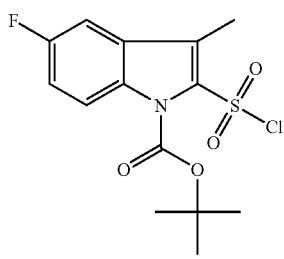

This compound was prepared in analogy to Example 28a starting from 5-fluoro-3-methyl-indole-1-carboxylic acid tert-butyl ester (1.0 g) in ether/THF 1:2 (15 ml), 1.7 N tert-BuLi (2.85 ml), SO$_2$-gas and NCS (0.59 g) to obtain the title compound (0.80 g) as a colorless solid. MS (EI): 347.2, 247.1 (M and M-Boc)

c) 2-(4-Bromo-2-trifluoromethyl-phenylsulfamoyl)-5-fluoro-3-methyl-indole-1-carboxylic acid tert-butyl ester

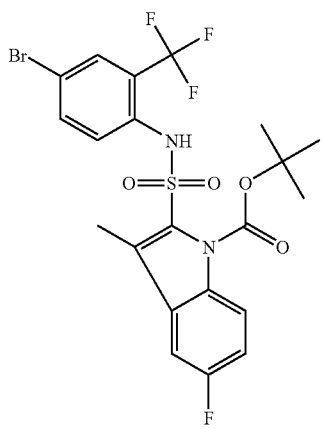

This compound was prepared in analogy to Example 1 starting from 2-chlorosulfonyl-5-fluoro-3-methyl-indole-1-carboxylic acid tert-butyl ester (0.29 g) and 2-amino-5-bromobenzotrifluoride (2.0 g) in pyridine (5 ml) by stirring for 7 days at rt to obtain the title compound (0.095 g) as a colorless foam. MS (ISN): 551.4, 549.3 (M−H)$^-$ d) 5-Fluoro-3-methyl-2-(4-pyridin-4-yl-2-trifluoromethyl-phenylsulfamoyl)-indole-1-carboxylic acid tert-butyl ester

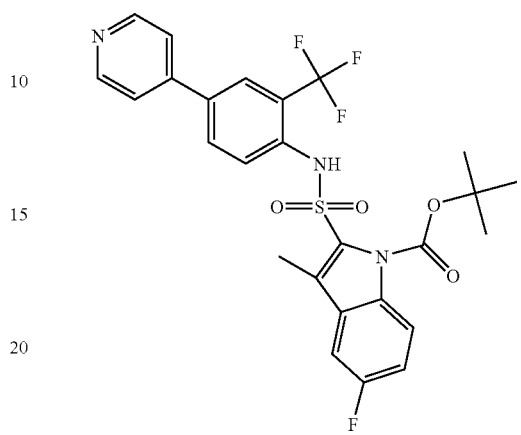

This compound was prepared in analogy to Example 2 starting from 2-(4-bromo-2-trifluoromethyl-phenylsulfamoyl)-5-fluoro-3-methyl-indole-1-carboxylic acid tert-butyl ester (0.108 g), 4-pyridineboronic acid (0.036 g) in 1,2-dimethoxyethane (5.0 ml), ethanol (0.4 ml) and 2 M aqueous sodium carbonate solution (0.8 ml) with tetrakis(triphenylphosphine)palladium (0.023 g) to obtain the desired compound (0.058 g) as a brownish foam. MS (ISN): 548.3 (M−H)$^-$ e) 5-Fluoro-3-methyl-1H-indole-2-sulfonic acid(4-pyridin-4-yl-2-trifluoromethyl-phenyl)-amide hydrochloride This compound was prepared in analogy to example 27b starting from 5-fluoro-3-methyl-2-(4-pyridin-4-yl-2-trifluoromethyl-phenylsulfamoyl)-indole-1-carboxylic acid tert-butyl ester (0.052 g), 2.5 N HCl/ethyl acetate (10.0 ml) to obtain the title compound (0.041 g) as a brownish amorphous powder. MS (ISN): 448.4 (M−H)$^-$

Example 30

5-Fluoro-1,3-dimethyl-1H-indole-2-sulfonic acid(4-pyridin-4-yl-2-trifluoromethyl-phenyl)-amide

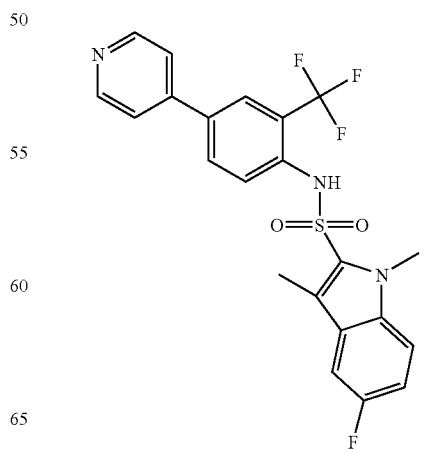

a) 5-Fluoro-1,3-dimethyl-1H-indole

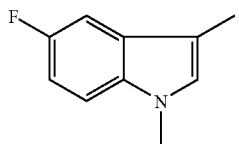

To a solution of 5-fluoro-3-methyl-indole (CAS: 392-13-2, 2.5 g) in DMF (20 ml) was added potassium hydroxide (1.41 g). The suspension was stirred at rt for 1 h and iodomethane (2.85 g) was added dropwise at 0-5° C. The reaction mixture was stirred at rt for 18 h and concentrated under high vacuum. The residue was quenched with water and extracted with ethyl acetate. The organics were washed, dried and concentrated. The crude residue was chromatographed on silica gel using heptane/ethyl acetate as eluent to obtain the desired compound (2.15 g) as a colorless liquid. MS (EI): 163.1 (M)

b) 5-Fluoro-1,3-dimethyl-1H-indole-2-sulfonyl chloride

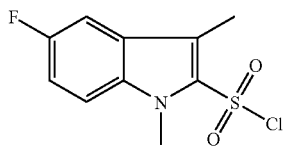

This compound was prepared in analogy to Example 28a starting from 5-fluoro-1,3-dimethyl-1H-indole (1.0 g) in ether/THF 1:2 (15 ml), 1.7 N tert-BuLi (4.33 ml), $SO_2$ gas and NCS (0.90 g) to obtain the title compound (0.27 g) as a yellowish solid. MS (ISN): 241.9 (M–F)

c) 5-Fluoro-1,3-dimethyl-1H-indole-2-sulfonic acid (4-bromo-2-trifluoromethyl-phenyl)-amide

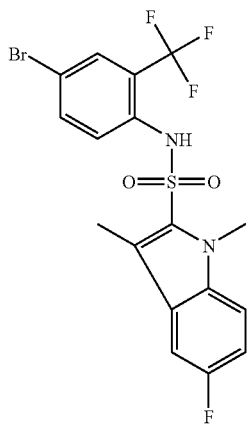

This compound was prepared in analogy to Example 1 starting from 5-fluoro-1,3-dimethyl-1H-indole-2-sulfonyl chloride (0.25 g) and 2-amino-5-bromobenzotrifluoride (2.3 g) in pyridine (5 ml) for 18 h at 35° C. to obtain the title compound (0.293 g) as a yellow solid. MS (ISN): 551.4, 549.3 (M–H)⁻ d) 5-Fluoro-1,3-dimethyl-1H-indole-2-sulfonic acid (4-pyridin-4-yl-2-trifluoromethyl-phenyl)-amide This product was prepared in analogy to Example 2 starting from 5-fluoro-1,3-dimethyl-1H-indole-2-sulfonic acid(4-bromo-2-trifluoromethyl-phenyl)-amide (0.100 g), 4-pyridineboronic acid (0.040 g) in 1,2-dimethoxyethane (5.0 ml), ethanol (1.0 ml) and 2 M aqueous sodium carbonate solution (1.0 ml) with tetrakis(triphenylphosphine)palladium (0.025 g) to obtain the title compound (0.058 g) as a brownish foam. MS (ISN): 462.4 (M–H)⁻

Example 31

5-Fluoro-3-isobutyl-benzo[b]thiophene-2-sulfonic acid(4-pyridin-4-yl-2-trifluoromethyl-phenyl)-amide

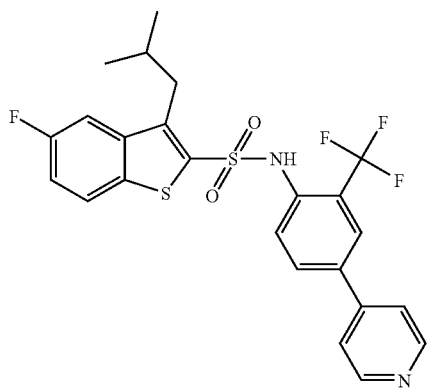

a) 5-Fluoro-3-isobutyl-benzo[b]thiophene

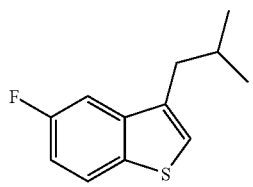

To a solution of 3-bromomethyl-5-fluorobenzothiophene (2.0 g; cf. Raga, Manuel; Palacin, Celia; Castello, Josep Maria; Ortiz, Jose A.; Cuberes, Maria Rosa; Moreno-Manas, Marcial, Eur. J. Med. Chem. (1986), 21(4), 329-32) in THF (30 ml) was added over 5 minutes isopropylmagnesium bromide (1.0 M, 16.6 ml). The reaction mixture was stirred at 50° C. for 5 h, cooled, quenched with ice/water and ammonium chloride solution, and extracted with ethyl acetate. The organic phases were washed with water, dried and concentrated. The residue was chromatographed on silica gel using heptane/methylene chloride as eluent to obtain the title compound (1.35 g) as a yellowish oil. MS (EI): 208.3 (M)

b) 5-Fluoro-3-isobutyl-benzo[b]thiophene-2-sulfonyl chloride

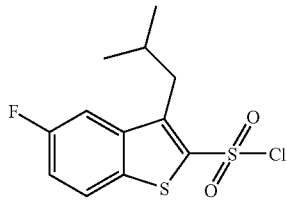

To a solution of 5-fluoro-3-isobutyl-benzo[b]thiophene (0.55 g) in chloroform (10 ml) was added chlorosulfonic acid (1.54 g), and the resulting mixture was stirred at rt for 3 h, quenched with ice/water, and extracted with methylene chloride. The organic phases were washed with water and aqueous sodium bicarbonate solution, dried and concentrated. The residue was chromatographed on silica gel using heptane/ethyl acetate as eluent to obtain the title compound (0.49 g) as a colorless oil. MS (EI): 306.8 (M)

c) 5-Fluoro-3-isobutyl-benzo[b]thiophene-2-sulfonic acid(4-bromo-2-trifluoromethyl-phenyl)-amide

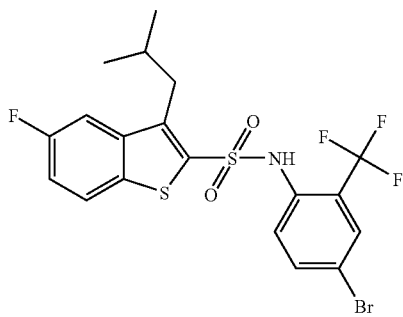

This compound was prepared in analogy to Example 1 starting from 5-fluoro-3-isobutyl-benzo[b]thiophene-2-sulfonyl chloride (044 g), 2-amino-5-bromobenzotrifluoride (3.44 g) in pyridine (5 ml) for 18 h at rt to obtain the desired compound (0.24 g) as a colorless solid. MS (ISN): 508.2, 510.3 (M−H)⁻ d) 5-Fluoro-3-isobutyl-benzo[b]thiophene-2-sulfonic acid(4-pyridin-4-yl-2-trifluoromethyl-phenyl)-amide This compound was prepared in analogy to Example 2 starting from 5-fluoro-3-isobutyl-benzo[b]thiophene-2-sulfonic acid(4-bromo-2-trifluoromethyl-phenyl)-amide (0.10 g) and 4-pyridineboronic acid (0.036 g) in 1,2-dimethoxyethane (7 ml), ethanol (1 ml) and 2 molar sodium carbonate (2.0 ml) with tetrakis(triphenylphosphine)palladium (0.027 g) to obtain the title compound (0.47 g) as a yellowish solid. MS (ISN): 507.1 (M−H)⁻

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | Ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of formula (I):

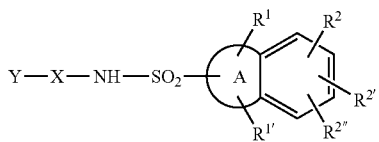

(I)

or a pharmaceutically acceptable salt thereof, wherein:

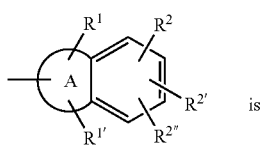 is

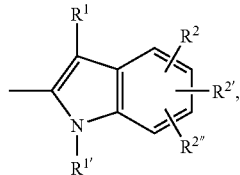

(a)

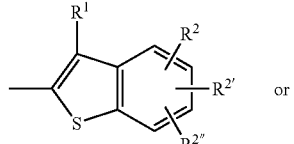

or (b)

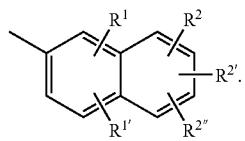

(c)

$R^1$ and $R^{1'}$ are independently selected from the group consisting of:
(1) hydrogen,
(2) halogen,
(3) nitro,
(4) cyano,
(5) amino,
(6) $C_{1-6}$ alkyl,
(7) heteroalkyl,
(8) $C_{3-7}$ cycloalkyl,
(9) $C_{2-6}$ alkenyl,
(10) $C_{2-6}$ alkynyl,
(11) hydroxy,
(12) $C_{1-6}$ alkoxy,
(13) —NR'R" or —($C_{0-6}$ alkylene)-NR'R", in which R' and R" are independently selected from the group consisting of hydrogen, $C_{1-6}$ alkyl, heteroalkyl, formyl, $C_{1-6}$ alkylcarbonyl, optionally substituted $C_{3-7}$ cycloalkylcarbonyl, optionally substituted arylcarbonyl, optionally substituted heteroarylcarbonyl, optionally substituted heterocyclylcarbonyl, $C_{1-6}$ alkylsulfonyl, optionally substituted $C_{3-7}$ cycloalkylsulfonyl, optionally substituted arylsulfonyl, optionally substituted heteroarylsulfonyl, and optionally substituted heterocyclylsulfonyl, and
(14) —($C_{0-6}$ alkylene)-OR', in which R' is hydrogen, $C_{1-6}$ alkyl, heteroalkyl, formyl or $C_{1-6}$ alkylcarbonyl,
wherein both $R^1$ and $R^{1'}$ exist or alternatively $R^1$ exists but $R^{1'}$ does not exist;
$R^2$, $R^{2'}$ and $R^{2''}$ are independently selected from the group consisting of hydrogen, halogen, cyano, nitro, amino, mono-$C_{1-6}$ alkyl substituted amino, di-$C_{1-6}$ alkyl substituted amino, $C_{1-6}$ alkyl, $C_{2-6}$ alkenyl, $C_{2-6}$ alkynyl, heteroalkyl, hydroxy, and $C_{1-6}$ alkoxy;
X is phenylene substituted by one, two or three substituents independently selected from the group consisting of halo $C_{1-6}$ alkyl, halo $C_{1-6}$ alkoxy, $C_{1-6}$ alkylsulfonyl, $C_{1-6}$ alkylsulfinyl, $C_{1-6}$ alkylthio, $C_{1-6}$ alkylsulfonyl-$C_{1-6}$ alkyl, $C_{1-6}$ alkylsulfinyl-$C_{1-6}$ alkyl, $C_{1-6}$ alkylthio-$C_{1-6}$ alkyl, acyl; and
Y is at the para position of X with respect to the —NH—SO$_2$— group and is selected from the group consisting of:
pyridyl, pyrimidinyl and piperidyl, optionally substituted by one or two substituents independently selected from the group consisting of halogen, C1-6 alkoxy and C1-6 alkoxycarbonyl.

2. A compound according to claim 1, wherein:

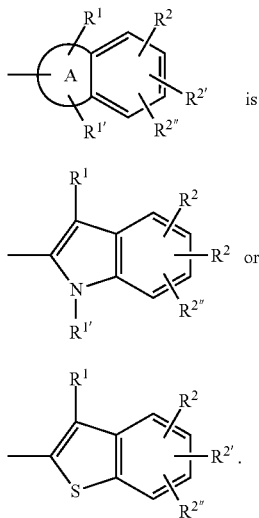

3. A compound according to claim 1, wherein:

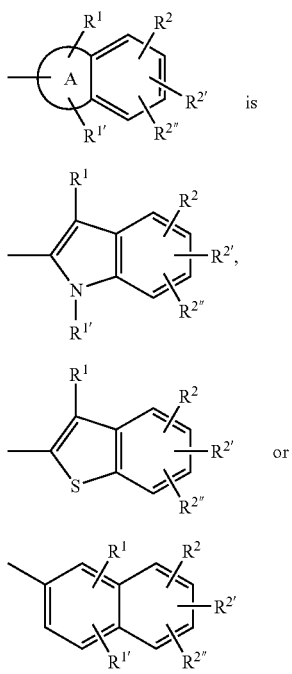

wherein $R^1$ and $R^{1'}$ are independently hydrogen or $C_{1-6}$ alkyl.

4. A compound according to claim 1, wherein:

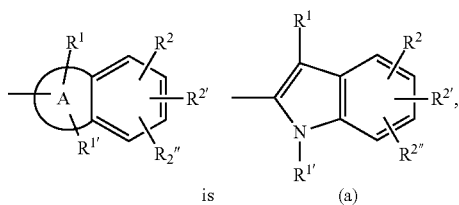

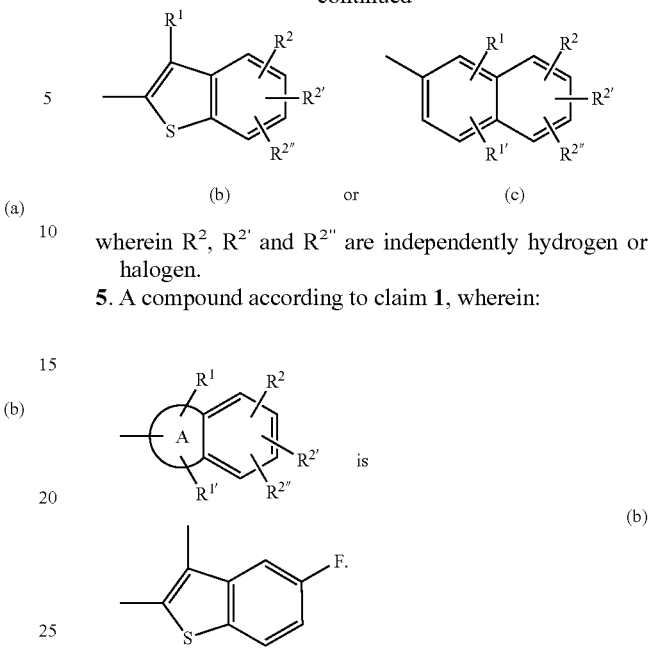

wherein $R^2$, $R^{2'}$ and $R^{2''}$ are independently hydrogen or halogen.

5. A compound according to claim 1, wherein:

6. A compound according to claim 1, wherein X is phenylene substituted by one, two or three substituents independently selected from the group consisting of halo $C_{1-6}$ alkyl, halo $C_{1-6}$ alkoxy, $C_{1-6}$ alkylsulfonyl, $C_{1-6}$ alkylsulfinyl, $C_{1-6}$ alkylthio, $C_{1-6}$ alkylsulfonyl-$C_{1-6}$ alkyl, $C_{1-6}$ alkylsulfinyl-$C_{1-6}$ alkyl, and $C_{1-6}$ alkylthio $C_{1-6}$ alkyl.

7. A compound according to claim 1, wherein X is phenylene substituted by halo $C_{1-6}$ alkyl or $C_{1-6}$ alkylsulfonyl at the ortho position with respect to the —NH—SO$_2$— group.

8. A compound according to claim 1, wherein X is phenylene substituted by trifluoromethyl or methylsulfonyl at the ortho position with respect to the —NH—SO$_2$— group.

9. 5-Fluoro-3-methyl-benzo[b]thiophene-2-sulfonic acid (4-pyridin-4-yl-2-trifluoromethyl-phenyl)-amide.

10. A compound according to claim 1, selected from the group consisting of:
   5-Fluoro-3-methyl-benzo[b]thiophene-2-sulfonic acid(4-pyridin-4-yl-2-trifluoromethyl-phenyl)-amide;
   5-Fluoro-3-methyl-benzo[b]thiophene-2-sulfonic acid[4-(2,6-difluoro-pyridin-4-yl)-2-trifluoromethyl-phenyl]-amide;
   5-Fluoro-3-methyl-benzo[b]thiophene-2-sulfonic acid[4-(3-fluoro-pyridin-4-yl)-2-trifluoromethyl-phenyl]-amide;
   5-Fluoro-3-methyl-benzo[b]thiophene-2-sulfonic acid[4-(2-fluoro-pyridin-4-yl)-2-trifluoromethyl-phenyl]-amide;
   5-Fluoro-3-methyl-benzo[b]thiophene-2-sulfonic acid(4-pyridin-3-yl-2-trifluoromethyl-phenyl)-amide;
   5-Fluoro-3-methyl-benzo[b]thiophene-2-sulfonic acid[4-(6-methoxy-pyridin-3-yl)-2-trifluoromethyl-phenyl]-amide;
   5-Fluoro-3-methyl-benzo[b]thiophene-2-sulfonic acid(4-pyrimidin-5-yl-2-trifluoromethyl-phenyl)-amide;
   5-Fluoro-3-methyl-benzo[b]thiophene-2-sulfonic acid[4-(2-methoxy-pyrimidin-5-yl)-2-trifluoromethyl-phenyl]-amide;
   5-Fluoro-3-methyl-benzo[b]thiophene-2-sulfonic acid[4-(5-fluoro-pyridin-3-yl)-2-trifluoromethyl-phenyl]-amide; and
any pharmaceutically acceptable salt thereof.

11. A compound according to claim 1, selected from the group consisting of:
- 5-Fluoro-3-methyl-benzo[b]thiophene-2-sulfonic acid[4-(6-fluoro-pyridin-3-yl)-2-trifluoromethyl-phenyl]-amide;
- 5-Fluoro-3-methyl-benzo[b]thiophene-2-sulfonic acid(2-methylsulfanylmethyl-4-pyridin-4-yl-phenyl)-amide;
- 5-Fluoro-3-methyl-benzo[b]thiophene-2-sulfonic acid(2-methanesulfinylmethyl-4-pyridin-4-yl-phenyl)-amide;
- 5-Fluoro-3-methyl-benzo[b]thiophene-2-sulfonic acid(2-methanesulfonylmethyl-4-pyridin-4-yl-phenyl)-amide;
- 5-Fluoro-3-methyl-benzo[b]thiophene-2-sulfonic acid(4-pyridin-4-yl-2-trifluoromethoxy-phenyl)-amide;
- 5-Fluoro-3-methyl-benzo[b]thiophene-2-sulfonic acid(4-pyridin-4-yl-phenyl)-amide,
- 5-Fluoro-3-methyl-benzo[b]thiophene-2-sulfonic acid(2-methanesulfonyl-4-piperidin-4-yl-phenyl)-amide hydrochloride; and
any pharmaceutically acceptable salt thereof.

12. A compound according to claim 1, selected from the group consisting of:
- 5-Fluoro-3-methyl-benzo[b]thiophene-2-sulfonic acid(2-methanesulfonyl-4-piperidin-4-yl-phenyl)-amide;
- Naphthalene-2-sulfonic acid(2-methanesulfonyl-4-pyridin-4-yl-phenyl)-amide;
- 5-Fluoro-3-methyl-benzo[b]thiophene-2-sulfonic acid(2-methanesulfonyl-4-pyridin-4-yl-phenyl)-amide;
- 4-[3-Methanesulfonyl-4-(1-methyl-1H-indole-2-sulfonylamino)-phenyl]-piperidine-1-carboxylic acid tert-butyl ester;
- 1-Methyl-1H-indole-2-sulfonic acid(2-methanesulfonyl-4-piperidin-4-yl-phenyl)-amide hydrochloride;
- 6-Fluoro-naphthalene-2-sulfonic acid(2-methanesulfonyl-4-pyridin-4-yl-phenyl)-amide;
- 1H-Indole-2-sulfonic acid(4-pyridin-4-yl-phenyl)-amide hydrochloride;
- 5-Fluoro-1-methyl-1H-indole-2-sulfonic acid(2-methanesulfonyl-4-piperidin-4-yl-phenyl)-amide hydrochloride;
- 5-Fluoro-1,3-dimethyl-1H-indole-2-sulfonic acid(4-pyridin-4-yl-2-trifluoromethyl-phenyl)-amide;
- 5-Fluoro-3-isobutyl-benzo[b]thiophene-2-sulfonic acid (4-pyridin-4-yl-2-trifluoromethyl-phenyl)-amide; and
any pharmaceutically acceptable salt thereof.

13. A pharmaceutical composition comprising a therapeutically effective amount of a compound of claim 1 and a pharmaceutically acceptable carrier.

14. A compound selected from the group consisting of:
- 5-Fluoro-3-methyl-benzo[b]thiophene-2-sulfonic acid(4-bromo-2-trifluoromethyl-phenyl)-amide;
- 5-Fluoro-3-methyl-benzo[b]thiophene-2-sulfonic acid(4-bromo-2-trifluoromethoxy-phenyl)-amide;
- 5-Fluoro-3-methyl-benzo[b]thiophene-2-sulfonic acid(2-ethyl-4-pyridin-4-yl-phenyl)-amide;
- 5-Fluoro-3-methyl-1H-indole-2-sulfonic acid (4-pyridin-4-yl-2-trifluoromethyl-phenyl)-amide hydrochloride;
- 5-Fluoro-3-methyl-benzo[b]thiophene-2-sulfonic acid[4-(1-oxy-pyridin-4-yl)-2-trifluoromethyl-phenyl]-amide; and
any pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,158,655 B2 | Page 1 of 1 |
| APPLICATION NO. | : 11/970628 | |
| DATED | : April 17, 2012 | |
| INVENTOR(S) | : Banner et al. | |

It is certified that error appears in the above-identified patent and that said Letters Patent is hereby corrected as shown below:

Cover page, column 2, under (74) Attorney, Agent or Firm
delete "Erian C. Remy" and insert -- Brian C. Remy --

Claim 1, column 40, line 66, delete "C1-6 alkoxy and C1-6" and insert -- $C_{1-6}$ alkoxy and $C_{1-6}$ --

Signed and Sealed this
Fifth Day of June, 2012

David J. Kappos
*Director of the United States Patent and Trademark Office*